United States Patent [19]

Herron et al.

[11] 4,319,028
[45] Mar. 9, 1982

[54] 7-(2-(SUBSTITUTED BENZOYL)AMINO)ACETAMIDO)CEPHALOSPORINS

[75] Inventors: David K. Herron; William H. W. Lunn, both of Indianapolis, Ind.

[73] Assignee: Eli Lilly and Company, Indianapolis, Ind.

[21] Appl. No.: 717,774

[22] Filed: Aug. 26, 1976

[51] Int. Cl.³ .......................................... C07D 501/52
[52] U.S. Cl. ...................... 544/26; 544/16; 544/24; 544/25; 544/27; 544/28; 544/29; 544/30; 548/259
[58] Field of Search ................ 260/243 C; 544/26, 27

[56] References Cited

U.S. PATENT DOCUMENTS 3,352,858 11/1967 Crast et al. ...................... 260/243 C
3,931,170 1/1976 Treuner et al. ................. 260/243 C

FOREIGN PATENT DOCUMENTS 833063 4/1976 Belgium .......................... 260/243 C

OTHER PUBLICATIONS

Iwanami et al., Chemical Abstracts, 1976, vol. 85: 160,128(f).

Primary Examiner—Paul M. Coughlan, Jr.
Attorney, Agent, or Firm—William B. Scanlon; Arthur R. Whale

[57] ABSTRACT

Cephalosporin antibiotics of the formula

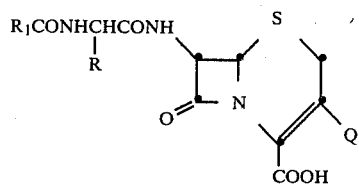

wherein R is cyclohexadienyl, phenyl or substituted phenyl, 2-thienyl, 3-thienyl, 2-furyl or 3-furyl; $R_1$ is a substituted phenyl having 1 to 4 hydroxy substituents or 1 to 3 amino substituents; and wherein Q is halo, methoxy, methyl or a group of the formula $-CH_2R_2$ wherein $R_2$ is alkanoyloxy, carbamoyloxy, alkoxy, halo, pyridinium or substituted pyridinium or a group of the formula $-SR_3$ wherein $R_3$ is alkyl, phenyl, substituted phenyl or a 5 or 6 membered-heteroaryl group having from 1 to 4 heteroatoms selected from the group consisting of O, S, and N;

are highly active broad spectrum antibiotics especially useful in the treatment of infections attributable to the gram-negative microorganisms.

37 Claims, No Drawings

7-(2-(SUBSTITUTED BENZOYL)AMINO)ACETAMIDO)CEPHALOSPORINS

SUMMARY OF THE INVENTION

Cephalosporin compounds having a high level of activity against both gram-positive and gram-negative pathogens are prepared from known 7-(substituted)-glycylamido cephalosporin compounds of the formula

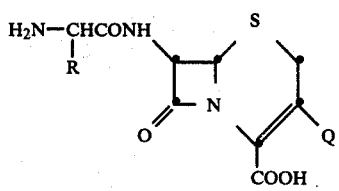

by acylating the free amino group of the 7-(substituted)-glyclamido side chain with the active ester

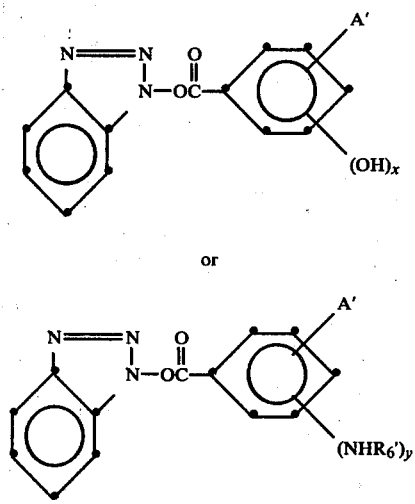

wherein X is 1, 2 or 3, and y is 1 or 2, and A' is a substituent selected from the group consisting of hydrogen, halo, protected amino, hydroxy, protected hydroxy, $C_1$–$C_4$ alkoxy, $C_1$–$C_4$ alkyl, nitro, cyano, methanesulfonamido, and trifluoromethyl, and $R_6'$ is an amino protecting group. For example 7-[D-[2-(4-hydroxyphenyl)-2-[(2,4-dihydroxybenzoylamino]acetyl]amino]-3-[[(5-methyl-1,3,4-thiadiazol-2-yl)-thio]methyl]-3-cephem-4-carboxylic acid is prepared by acylating 7-[D-[2-(4-hydroxyphenyl)-2-aminoacetyl]amino-3-[[(5-methyl-1,3,4-thiadiazol-2-yl)thio]methyl]-3-cephem-4-carboxylic acid with 1'-benzotriazolyl 2,4-dihydroxybenzoate derived from 2,4-dihydroxybenzoic acid, 1-hydroxybenzotriazole, and dicyclohexylcarbodiimide. The new cephalosporins described herein are active against a broad spectrum of microorganisms and accordingly are useful in combating infections in warm-blooded animals when administered parenterally.

The cephalosporins described herein can be converted to the biologically active esters, for example, pivaloyloxymethyl or acetoxymethyl esters and to the pharmaceutically useful salts such as the sodium and potassium salt.

DESCRIPTION OF THE PRIOR ART

A number of cephalosporin compounds having an acylated amino group in the α-position of the 7-acylamino group have been described. Most prominent of such compounds in the prior art are the α-ureidocephalosporanic acids. See, for example, U.S. Pat. Nos. 3,673,183, 3,708,479, and 3,646,024. Similarly substituted penicillins have also been disclosed (U.S. Pat. Nos. 3,697,507 and 3,634,405). More recently a number of α-heteroaroylamino penicillins have been disclosed (Belgian Pat. Nos. 828,692 and 821,243; West German Pat. Nos. 2,461,526; 2,448,966 and 2,450,668; Ger. Offen. 2,347,533 and 2,416,449; Japanese published application Nos. 25586/73, 10733/75, 85102/74 and 85103/74; and U.S. Pat. No. 3,945,995). 6-[α-Substituted benzoylamino-α-aryl]acetamido penicillins are described in Japanese published application No. 121,292/75. 7-[α-Heteroaroylamino-α-aryl]acetamido cephalosporins, apparently the closest art relevant to the novel cephalosporin compounds disclosed herein, have been described in Belgian Pat. No. 828,933, and in German Offenlegungsschrift Nos. 2,520,561 and 2,544,243.

DETAILED DESCRIPTION OF THE INVENTION

This invention is directed to new cephalosporin antibiotic compounds represented by the following general formula

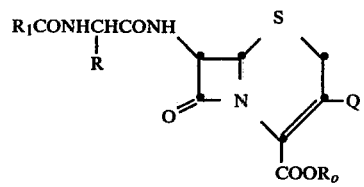

wherein Q is chloro, bromo, methoxy, methyl or a group of the formula —$CH_2R_2$
wherein $R_2$ is
(a) $C_2$–$C_4$ alkanoyloxy;
(b) carbamoyloxy or $C_1$–$C_4$ alkylcarbamoyloxy;
(c) $C_1$–$C_4$ alkoxy;
(d) chloro or bromo;
(e) pyridinium or substituted pyridinium wherein the substituent is selected from the group consisting of $C_1$–$C_4$ alkyl, halo, hydroxy, hydroxymethyl, trifluoromethyl, carbamoyl, $C_1$–$C_4$ alkylcarbamoyl, carboxy, cyano, and acetyl;
(f) a group of the formula —$SR_3$
wherein $R_3$ is
(a) $C_1$–$C_4$ alkyl, phenyl or phenyl substituted with 1 or 2 groups selected from the group consisting of $C_1$–$C_4$ alkyl, $C_1$–$C_4$ alkoxy, halo, hydroxy, nitro, cyano, methanesulfonamido and trifluoromethyl;
(b) a tetrazolyl group selected from the group consisting of

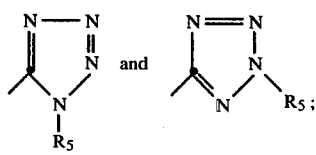

(c) a thiadiazolyl group selected from the group consisting of

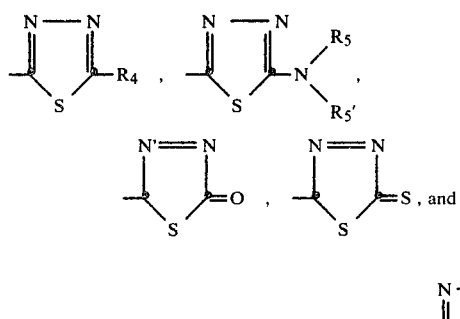

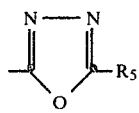

(d) an oxadiazolyl group of the formula (e) a triazolyl group selected from the group consisting of

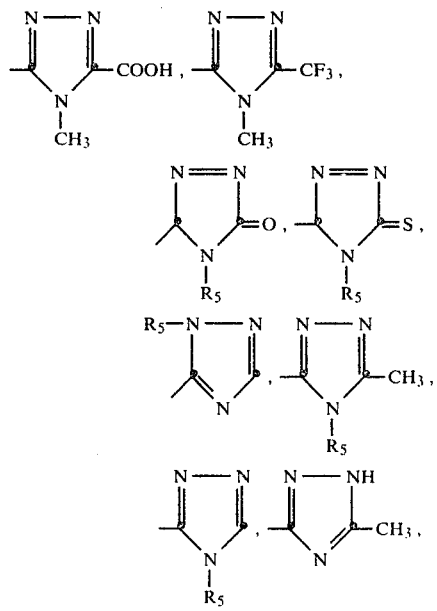

(f) a thiazolyl group selected from the group consisting of

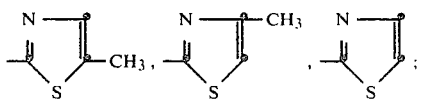

(g) an isothiazolyl group of the formula

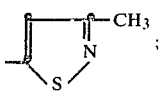

(h) an oxazolyl group of the formula

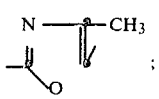

(i) a triazinyl group of the formula

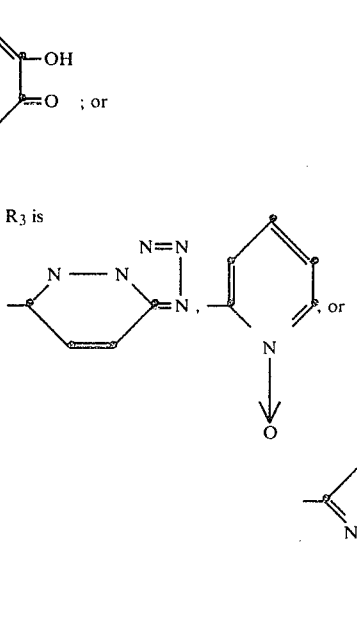

wherein in the above formulas $R_4$ is hydrogen, $C_1$–$C_4$ alkyl, aminomethyl, protected aminomethyl or hydroxymethyl, and $R_5$ and $R_5'$ are hydrogen or $C_1$–$C_4$ alkyl; and R is cyclohexadienyl, phenyl or phenyl substituted with 1 or 2 groups selected from the group consisting of $C_1$–$C_4$ alkyl, $C_1$–$C_4$ alkoxy, halo, hydroxy, protected hydroxy, nitro, cyano, methanesulfonamido and trifluoromethyl; or R is 2-thienyl, 3-thienyl, 2-furyl or 3-furyl; and $R_1$ is a group of the formula

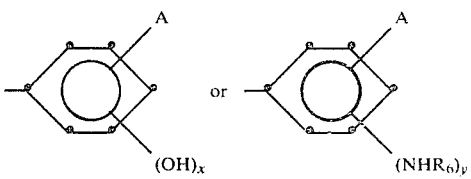

wherein X is 1, 2, or 3, and y is 1 or 2, and wherein A is a substituent selected from the group consisting of hydrogen, halo, $C_1$–$C_4$ alkoxy, amino, protected amino, hydroxy, protected hydroxy, $C_1$–$C_4$ alkyl, nitro, cyano, methanesulfonamido and trifluoromethyl, and $R_6$ is hydrogen or an amino protecting group; and $R_o$ is hydrogen, indanyl, phthalidyl or an acyloxymethyl group of the formula

wherein Y' is $C_1$–$C_4$ alkyl or phenyl; and when $R_o$ is hydrogen, the pharmaceutical acceptable non-toxic salts of the acids represented thereby.

In the foregoing definition of the compounds of the present invention "halo" refers to fluoro, chloro or bromo, preferably chloro. The term "$C_1$–$C_4$ alkanoyloxy" as used herein encompasses acetoxy, propionyloxy, butyryloxy, isobutyryloxy and like groups. Representative of "$C_1$–$C_4$ alkylcarbamoyloxy" are methylcarbamoyloxy, ethylcarbamoyloxy, N,N-dimethylcarbamoyloxy, isopropylcarbamoyloxy and the like.

The term "$C_1$–$C_4$ alkoxy" refers to methoxy, ethoxy, propoxy, isopropoxy, n-butoxy, isobutoxy and sec-butoxy. "$C_1$–$C_4$ alkyl" refers to methyl ethyl, propyl, isopropyl, n-butyl, iso-butyl, tert-butyl, and sec-butyl.

Representative of the substituted pyridinium groups defined in the foregoing description are 2-methylpyridinium, 3-methylpyridinium, 4-methylpyridinium, 3-ethylpyridinium, 4-propylpyridinium, 3-hydroxypyridinium, 4-hydroxymethylpyridinium, 3-fluoropyridinium, 3-chloropyridinium, 4-trifluoromethylpyridinium, 3-carbamoylpyridinium, 4-carbamoylpyridinium, 4-methylcarbamoylpyridinium, 3-cyanopyridinium, 3-acetylpyridinium and 4-acetylpyridinium.

Illustrative of the C-3 substituents represented by the group —$CH_2SR_3$ wherein $R_3$ is $C_1$–$C_4$ alkyl, phenyl, or substituted phenyl are methylthiomethyl, propylthiomethyl, phenylthiomethyl, 4-methylphenylthiomethyl, 4-chlorophenylthiomethyl, 2-bromophenylthiomethyl, 3-nitrophenylthiomethyl, 2-methoxyphenylthiomethyl, 3-cyanophenylthiomethyl, 3,4-dichlorophenylthiomethyl, 4-methanesulfonamidophenylthiomethyl, 4-trifluoromethylphenylthiomethyl, 3-chloro-4-hydroxyphenylthiomethyl and 3-methyl-4-chlorophenylthiomethyl.

Representative of $R_3$ when $R_3$ is a tetrazolyl group are 1-methyltetrazol-5-yl, 1-isopropyltetrazol-5-yl, 2-ethyltetrazol-5-yl, 2-hydroxymethyltetrazol-5-yl, 5-tetrazolyl, 1-tert-butoxycarbonyl aminomethyltetrazol-5-yl, 2-methyltetrazol-5-yl, 1-hydroxymethyltetrazol-5-yl and 1-ethyltetrazol-5-yl.

Representative of $R_3$ when $R_3$ is a thiadiazolyl group are 2-methyl-1,3,4-thiadiazol-5-yl, 1,3,4-thiadiazol-5-yl, 2-(N,N-dimethylamino)-1,3,4-thiadiazol-5-yl, 2-oxo-1,3,4-(5H)thiadiazol-5-yl, 2-thioxo-1,3,4-(5H)thiadiazol-5-yl, and 3-methyl-1,2,4-thiadiazol-5-yl.

As defined hereinabove $R_3$ can be an oxadiazolyl group; illustrative of such groups are 1,3,4-oxadiazol-5-yl, 2-methyl-1,3,4-oxadiazol-5-yl and 2-ethyl-1,3,4-oxadiazol-5-yl.

Representative of $R_3$ when $R_3$ is a triazolyl group are 1-methyl-2-carboxy-1,3,4-triazol-5-yl, 1-methyl-2-trifluoromethyl-1,3,4-triazol-5-yl, 1-methyl-2-oxo-1,3,4-(5H)triazol-5-yl, 1-propyl-2-oxo-1,3,4-(5H)triazol-5-yl, 1-methyl-2-thioxo-1,3,4-(5H)triazol-5-yl, 4-methyl-1,3,4-triazol-5-yl, 1-ethyl-2-methyl-1,3,4-triazol-5-yl, 1-methyl-2-methyl-1,3,4-triazol-5-yl, 2-methyl-1,3,4-(1H)-triazol-5-yl, 1,3,4-(1H)triazol-2-yl, 1-methyl-1,3,4-triazol-5-yl, 1-butyl-1,3,4-triazol-5-yl, 2-methyl-1,3,4-(3H)triazol-5-yl, 2-methyl-1,3,4-(2H)triazol-5-yl, 1,2,3-(1H)triazol-5-yl, 1-methyl-1,2,3-triazol-5-yl and 1-ethyl-1,2,3-triazol-5-yl.

Illustrative of R in the foregoing description of the present invention where R is a substituted phenyl group are 4-hydroxyphenyl, 3-hydroxyphenyl, 4-hydroxy-3-chlorophenyl, 4-methylphenyl, 3-butylphenyl, 4-methoxyphenyl, 2-bromo-3-methoxyphenyl 4-benzyloxyphenyl, 3-methanesulfonamidophenyl, 4-methanesulfonamidophenyl, 3-nitrophenyl, 4-trifluoromethylphenyl, 3-cyanophenyl and like groups.

The term "protected amino" as employed in the above definition has reference to an amino group substituted with one of the commonly employed amino blocking groups ("amino protecting groups" herein) such as the tert-butoxycarbonyl group (t-BOC); the benzyloxycarbonyl group, the 4-methoxybenzyloxycarbonyl group, the 4-nitrobenzyloxycarbonyl group, or the 2,2,2-trichloroethoxycarbonyl group. Like conventional amino protecting groups such as those described in J. W. Barton in "Protective Groups in Organic Chemistry," J. F. W. McOmie, Ed., Plenum Press, New York, N.Y., 1973, Chapter 2 shall be recognized as suitable.

The term "protected hydroxy" has reference to the readily cleavable groups formed with an hydroxyl group such as the formyloxy group, the chloroacetoxy group, the benzyloxy group, the benzhydryloxy group, the trityloxy group, the 4-nitrobenzyloxy group, the trimethylsilyloxy group, the phenacyloxy group, the tert-butoxy group, the methoxymethoxy group, the tetrahydropyranyloxy group, and the like. Other "hydroxy protecting groups," including those described by C. B. Reese in "Protective Groups in Organic Chemistry", supra, Chapter 3 shall be considered as within the term "protected hydroxy" as used herein.

In the foregoing definitions, hydroxy and amino protecting groups are not exhaustively defined. The function of such groups is to protect the reactive functional groups during the preparation of the desired products and then be removed without disrupting the remainder of the molecule. Many such protective groups are well known in the art and the use of other groups equally applicable to the compounds of the present invention shall be recognized as suitable. Thus, there is no novelty or inventiveness asserted with regard to the "protecting groups" alluded to in this specification, nor is it intended that the invention be limited by the groups specifically disclosed herein.

The formula

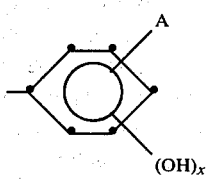

defining $R_1$ in the above description of the compounds of the present invention refers to 2-hydroxyphenyl, 3-hydroxyphenyl, 4-hydroxyphenyl, 2,3-dihydroxyphenyl, 3,4-dihydroxyphenyl, 2,4-dihydroxyphenyl, 2,3,4-trihydroxyphenyl, 3,4,5-trihydroxyphenyl, 2,3,5-trihydroxyphenyl, 2,3,4,5-tetrahydroxyphenyl, 2,3,5,6-tetrahydroxyphenyl, 3-chloro-2,4-dihydroxyphenyl, 2-amino-3-hydroxyphenyl, 2-bromo-3,4-dihydroxyphenyl, 3-methoxy-4-hydroxyphenyl, 4-methyl-2-hydroxyphenyl, 3-methanesulfonamido-4-hydroxyphenyl, 4-methanesulfonamido-3-hydroxyphenyl, 3-amino-4-hydroxyphenyl, 3-methanesulfonamido-2,4-dihydroxyphenyl, 3-cyano-4-hydroxyphenyl, 4-trifluoromethyl-2,3-dihydroxyphenyl, 5-(tert-butoxycarbonylamino)-2-hydroxyphenyl, and like hydroxy substituted phenyl groups.

The formula

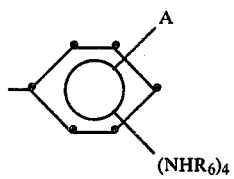

defining $R_1$ in the above description of the compounds of the present invention refers to 2-aminophenyl, 3-aminophenyl, 4-aminophenyl, 4-(4-methoxybenzyloxycarbonylamino)phenyl, 2,5-diaminophenyl, 3,4-diaminophenyl, 3,5-di(4-nitrobenzyloxycarbonylamino)phenyl, 2,3,5-triaminophenyl, 3,4,5-tri(tert-butoxycarbonylamino)phenyl, 3,5-diamino-2-hydroxyphenyl, 3,5-diamino-4-hydroxyphenyl, 4,5-di(tert-butoxycarbonylamino)-2-hydroxyphenyl, 2-amino-3-bromophenyl, 2-amino-5-chlorophenyl, 2-amino-3-iodophenyl, 3-amino-2-methoxyphenyl, 4-amino-3-methoxyphenyl, 3-amino-5-nitrophenyl, 2-amino-4-methylphenyl, and like amino or protected amino substituted phenyl groups.

The cephalosporin antibiotic compounds of the present invention are prepared by acylation of cephalosporin compounds of the formula

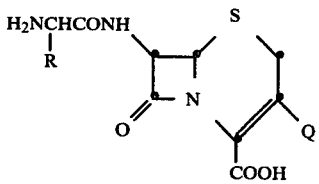

wherein Q and R are as defined herein above. Such starting materials are well known in the cephalosporin art. The α-amino-α-(substituted)acetamido side chain, common to all of the starting materials for the compounds of the present invention, is typically disclosed as a side chain substituent in patents and other publications directed to the preparation of "new" cephalosporin compounds. Thus, for example starting materials of the above formula wherein R is phenyl, substituted phenyl or thienyl and wherein Q is a 1-lower alkyltetrazol-5-ylthiomethyl group or a 5-lower alkyl-1,3,4-thiadiazol-2-ylthiomethyl group are described in U.S. Pat. No. 3,641,021. Starting materials having a 3-chloro or a 3-bromo group are described in U.S. Pat. No. 3,925,372. The following table shows the source of other starting materials available for the preparation of the 7-[α-[(hydroxy substituted aroyl)-amino]acetamido]cephalosporin compounds of the present invention.

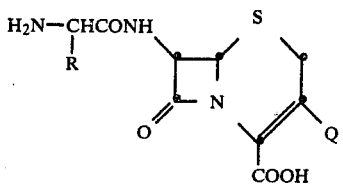

| Q | Source |
|---|---|
| —OCH₃ | U.S. Pat. No. 3,917,588 |
| —CH₃ | cephalexin |
| —CH₂OCCH₃ (O) | cephaloglycin |
| —CH₂S—[N—NR' / Z / A], Z = S or NH or N—alkyl, A = O or S | Belgian Patent 807,011<br>U.S. Pat. No. 3,946,005<br>U.S. Pat. No. 3,957,768<br>U.S. Pat. No. 3,899,394 |
| —CH₂S—[ring with N, N-H] | |
| —[N—CH₃ / S ring / O] | U.S. Pat. No. 3,687,945 |
| —[S-pyridone-N-O ring] | U.S. Pat. No. 3,775,408 |
| —S—[N—N / O ring] | Belgian Patent 816,745 |

Exemplary of the starting materials which are acylated to provide the novel compounds of the present invention are 7-[D-[(2-phenyl-2-amino)acetyl]amino]-3-methoxy-3-cephem-4-carboxylic acid, 7-[D-[2-(4-hydroxyphenyl)-2-aminoacetyl]amino]-3-chloro-3-cephem-4-carboxylic acid, 7-[D-[2-(3-chloro-4-hydroxyphenyl)-2-aminoacetyl]amino]-3-pyridiniummethyl-3-cephem-4-carboxylic acid, 7-[D-[2-(2-thienyl)-aminoacetyl]amino]-3-[[(1-methyltetrazol-5-yl)thio]methyl]-3-cephem-4-carboxylic acid, 7-[D-[2-(1,4-cyclohexadienyl)-2-aminoacetyl]amino]-3-methyl-3-cephem-4-carboxylic acid, 7-[D-[2-phenyl-2-aminoacetyl]amino]-3-carbamoyloxymethyl-3-cephem-4-carboxylic acid, 7-[D-[2-(2-furyl)-2-aminoacetyl]amino]-3-[(4-carboxamidopyridinium)methyl]-3-cephem-4-carboxylic acid, 7-[D-[2-(4-hydroxyphenyl)-2-aminoacetyl]amino]-3-phenylthiomethyl-3-cephem-4-carboxylic acid, 7-[D-[2-(4-methylphenyl)-2-aminoacetyl]amino]-3-bromo-3-cephem-4-carboxylic acid, 7-[D-[2-phenyl-2-aminoacetyl]amino]-3-[[(2-oxo-1,3,4-(5H)thiadiazol-5-yl)thio]methyl-3-cephem-4-carboxylic acid, 7-[D-[2-(4-hydroxymethyl)-2-aminoacetyl]amino]-3-methylthiomethyl-3-cephem-4-carboxylic acid, 7-[D-[2-(2-methoxyphenyl)-2-aminoacetyl]amino]-3-[[(5-tetrazolyl)thio]methyl]-3-cephem-4-carboxylic acid, 7-[D-[2-(3-nitrophenyl)-2-aminoacetyl]amino]-3-[[(1-hydroxymethyltetrazol-5-yl)thio]methyl]-3-cephem-4-carboxylic acid, 7-[D-[2-(3-methanesulfonamidophenyl)-2-aminoacetyl]amino]-3-[[(3-methyl-1,2,4-thiadiazol-5-yl)thio]methyl]-3-cephem-4-carboxylic acid, 7-[D-[2-(4-hydroxyphenyl)-2-aminoacetyl]amino]-3-[[(1-methyltetrazol-5-yl)thio]methyl]-3-cephem-4-carboxylic acid, 7-[D-[2-phenyl-2-aminoacetyl]amino]-3-[[(4-methyl-1,3,4-triazol-5-yl)thio]methyl]-3-cephem-4-carboxylic acid, 7-[D-[2-(2-thienyl)-2-aminoacetyl]amino]-3-[[(1-methyl-1,2,3-triazol-5-yl)thio]methyl]-3-cephem-4-carboxylate, 7-[D-[2-(3-thienyl)-2-aminoacetyl]amino]-3-acetoxymethyl-3-cephem-4-carboxylic acid, 7-[D-[2-phenyl-2-aminoacetyl]amino]-3methoxymethyl-3-cephem-4-carboxylic acid, 7-[D-[2-(4-hydroxyphenyl)-2-aminoacetyl]amino]-3-chloromethyl-3-cephem-4-carboxylic acid, 7-[D-[2-(4-hydroxyphenyl)-2-aminoacetyl]amino]-3-[[(4,5,-dihydro-6-hydroxy-4-methyl-5-oxo-1,2,4-triazin-3-yl)thio]methyl]-3-cephem-4-carboxylic acid, 7-[D-[2-phenyl-2-aminoacetyl]amino]-3-[[(4-methyloxazol-2yl)thio]methyl]-3-cephem-4-carboxylic acid, and 7-[D-[2-phenyl-2-aminoacetyl]amino]-3-[[(5-methylthiazol-2-yl)thio]methyl]-3-cephem-4-carboxylic acid.

These starting materials are typically prepared from the corresponding compounds having the α-amino group on the C7-side chain protected with one of the conventional amino protecting groups; the tert-butoxycarbonyl amino-protecting-group is most common. Thus, for example, 7-[D-[2-(2-thienyl)-2-aminoacetyl]amino]-3-chloro-3-cephem-4-carboxylic acid, isolated as its trifluoroacetic acid addition salt, is prepared by the reaction of 7-[D-[2-(2-thienyl)-2-(tert-butoxycarbonylamino)acetyl]amino]-3-chloro-3cephem-4-carboxylic acid with trifluoroacetic acid. The acid addition salts (eg. the trifluoroacetic acid salt or the hydrochloride salt) of the aforedescribed starting materials are also conveniently employed as starting materials in the preparation of the cephalosporin compounds of this invention.

To prepare the compounds of the present invention, the aforedescribed starting materials, generally 7-(substituted)glycylamidocephalosporin compounds are acylated at the free amino group of the substituted glycylamido side chain with an active ester of the formula

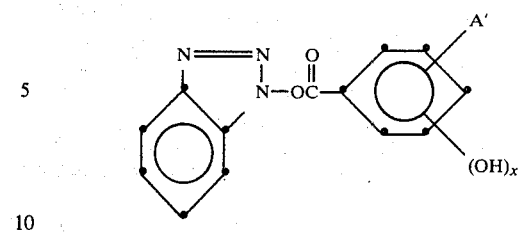

or

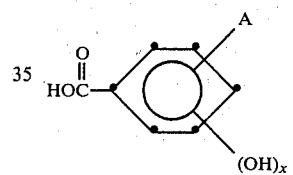

wherein X is 1, 2 or 3; y is 1 or 2; A' is a substituent selected from the group consisting of hydrogen, halo, protected amino, hydroxy, protected hydroxy $C_1$–$C_4$ alkoxy, $C_1$–$C_4$ alkyl, nitro, cyano, methanesulfonamido, and trifluoromethyl; and wherein $R_6'$ is an amino protecting group.

The active esters used in preparing the compounds of the present invention are derived from known substituted benzoic acids of the formula wherein x, y and A are as defined hereinabove. Those benzoic acids having 1 or more amino substituents are, prior to the preparation of their active ester derivatives, protected at the amino group(s) by any one of a number of the known amino protecting groups, including among others tert-butoxycarbonylamino, 4-methoxybenzyloxycarbonyl, 4-nitrobenzyloxycarbonyl, benzyloxycarbonyl, and 2,2,2-trichloroethoxycarbonyl; the amino protecting groups are removed subsequent to the active-ester acylation of the 7-(substituted)-glycylaminocephalosporin by using well-known conventional laboratory techniques.

Exemplary of benzoic acid starting materials used for the preparation of the compounds of the present invention are 2-hydroxybenzoic acid, 3-hydroxybenzoic acid, 4-hydroxybenzoic acid, 2,3-dihydroxybenzoic acid, 3,4-dihydroxybenzoic acid, 2-chloro-4-hydroxybenzoic acid, 3-nitro-4-hydroxybenzoic acid, 3-methanesulfonamido-2,4-dihydroxybenzoic acid, 2,4,6-trihydroxybenzoic acid, 4-methoxy-2,6-dihydroxybenzoic acid, 2,3,4,6-tetrahydroxybenzoic acid, 2-methyl-4,6-dihydroxybenzoic acid, 3-cyano-2,6-dihydroxybenzoic acid, 2-aminobenzoic acid, 3-aminobenzoic acid, 2,5-diaminobenzoic acid, 2,4,6-triaminobenzoic acid, 3,4,5-triaminobenzoic acid, 3,5-diamino-2-hydroxybenzoic acid, 4,5-diamino-2-ethoxybenzoic acid, 2-amino-3-hydroxybenzoic acid, 3-amino-4-methoxybenzoic acid, 2-amino-5-bromobenzoic acid, 4-amino-2-chorobenzoic acid, 3-amino-5-nitrobenzoic acid, 2-amino-4-methylbenzoic acid and 3-methanesulfonamido-4-aminobenzoic acid.

The substituted benzoic acid active esters, used as acylating agents in the preparation of the compounds of this invention, are prepared by reacting the substituted benzoic acid (with amino substitutents, if present, protected by a conventional amino protecting group) with an equivalent amount of 1-hydroxybenzotriazole monohydrate (HBT) in the presence of an equivalent amount of dicyclohexylcarbodiimide (DCC) in dry tetrahydrofuran at 0° C. Typically the dicyclohexylcarbodiimide is added in solution to a solution of the substituted benzoic acid and the 1-hydroxybenzotriazole monohydrate under nitrogen at about 0° C. After the reaction mixture is allowed to stir at room temperature for about 2 hours, the dicyclohexylurea, formed as a by-product in the active ester formation, is filtered from the reaction mixture. The filtrate thereby obtained either can be evaporated in vacuo to dryness to provide the active ester intermediate or it can be used directly in the acylation of a 7-(substituted)glycylaminocephalosporin to provide the compounds of the present invention. Thus, 1'-benzotriazolyl 3,6-dihydroxybenzoate is prepared by (a) adding a solution of 1 equivalent of dicyclohexylcarbodiimide in dry tetrahydrofuran to a mixture of 1 equivalent of 3,6-dihydroxybenzoic acid and 1 equivalent of 1-hydroxybenzotriazole monohydrate in tetrahydrofuran under a nitrogen atmosphere at about 0° C.; (b) stirring the reaction mixture at room temperature for two hours; and (c) filtering the reaction mixture and evaporating the filtrate in vacuo to dryness.

Where the substituted benzoic acid starting material has 1 or more amino substituents, such benzoic acids are first protected by a conventional amino protecting group(s). Thus, for example, when 4,5-diamino-2-hydroxybenzoic acid is used as the starting material,— for the preparation of a 7-[D-[2-(substituted)-2-[(4,5-diamino-2-hydroxybenzoyl)-amino]acetyl]amino]cephalosporin—prior to the preparation of the benzotriazolyl active ester, the amino groups are first protected using conventional laboratory procedures with, for example, the tert-butyloxycarbonyl group employing tert-butyl chloroformate or tert-butyloxycarbonyl azide. The resulting 4,5-di-tert-butoxycarbonylamino-2-hydroxybenzoic acid is then converted to its 1-benzotriazolyl active ester in accordance with the aforedescribed procedure using 1-hydroxybenzotriazole monohydrate and dicyclohexylcarbodiimide. Acylation of a substrate 7-(substituted)D-glycylaminocephalosporin with the active ester thereby obtained provides a 7-[D-[2-(substituted)-2-[(4,5-di-tert-butoxycarbonylamino-2-hydroxybenzoyl)amino]acetyl]amino]-cephalosporin which is then "deblocked" using standard laboratory procedures to provide a 7-[D-[2-substituted)-2-[(4,5-diamino-2-hydroxybenzoyl)amino]acetyl]amino]cephalosporin compound of the present invention.

The acylation of the abovedescribed substrate 7-[D-[2-(substituted)-2-aminoacetyl]amino]cephalosporin derivatives to provide the compounds of the present invention is typically carried out as a two-step process comprising (1) silylation of the substrate cephalosporin (or its acid addition salt) with a silylating agent to provide the corresponding cephalosporin silyl ester, thus protecting the $C_4$-carboxy groups; and (2) reacting the silylated cephalosporin substrate with the aforedescribed 1-benzotriazolyl active esters.

The silylation step is conveniently carried out in dry acetonitrile at about 0° C. and to insure anhydrous conditions, under an atmosphere of a dry inert gas such as nitrogen or argon. Generally an excess of a silylating agent such as bis-(trimethylsilyl)-acetamide (BSA) is reacted with the cephalosporin substrate suspended in dry acetonitrile at about 0° C. The reaction mixture is stirred at about 0° C. until homogeneous, usually after 5 to 30 minutes. The silylated substrate cephalosporin, a 7-[D-[2-(substituted)-2-aminoacetyl]amino]cephalosporin silyl ester, is isolated by evaporation in vacuo of the reaction medium and the excess silylating agent. Thus, for example, trimethylsilyl 7-[D-[2-(4-hydroxyphenyl)-2-aminoacetyl]-amino]-3-[[(1-methyl-1,3,4-triazol-2-yl)thio]methyl]-3-cephem-4-carboxylate is prepared from the trifluoroacetic acid addition salt of 7-[D-[2-(4-hydroxyphenyl)-2-aminoacetyl]amino]-3-[[(1-methyl-1,3,4-triazol-2-yl)thio]methyl]-3-cephem-4-carboxylic acid by suspending the acid addition salt in 8 ml. of dry acetonitrile under a nitrogen atmosphere; cooling to about 0° C.; adding 1 ml. of BSA to the suspension; and thereafter the evaporating the reaction medium to dryness when the reaction mixture appears to be homgeneous.

Typically the silylated cephalosporin substrate, prepared and isolated as described above, is then acylated with the desired benzotriazolyl substituted-benzoate by adding a tetrahydrofuran solution of the silylated cephalosporin to a cooled tetrahydrofuran solution of an equivalent amount of the active ester. The acylation reaction mixture is then stirred at room temperature for about 12 to about 24 hours, after which time the reaction mixture is evaporated in vacuo to dryness. The product thereby obtained, a substituted cephem acid compound of the present invention, is isolated and purified using conventional laboratory techniques, the particular isolation and purification procedures employed being dependent essentially upon the solubility characteristics, crystallinity, stability, $pK_a$ and like physical properties of the product compound. Where the product does not display unusual water solubility, a standard acid-base extraction work-up procedure is suitable for the isolation-purification of the product cephalosporin derivatives. Where such a standard procedure is found to be not applicable to a particular product, successive aqueous/nonaqueous triturations of the impure product have proved to be successful purification technique.

Where the products isolated and purified in accordance with the abovedescribed procedures bear protected amino or protected hydroxy substituents, an additional "deblocking" step is required to prepare the claimed biologically active cephem compounds of the present invention. The particular reactions condition employed for this deblocking step is dependent upon the nature of the protecting groups present on the substrate cephalosporin, and those skilled in the art will know what reaction conditions are necessary to effectuate the removal of the protecting group and the recovery of the "deblocked" substrate. Thus, while treatment with trifluoroacetic acid will effect removal of the tert-butoxycarbonyl or the 4-methoxybenzyloxycarbonyl group, reducing reaction conditions, for example, hydrogenation in the presence of a palladium catalyst, are required for the removal of the 4-nitrobenzyloxycarbonyl protecting group.

According to the above-described preparative procedures the 7-[D-[2-(substituted)-2-[(amino-substituted benzoyl)amino]acetyl]amino]cephalosporin derivatives of the present invention are prepared by (1) blocking the amino-substituted benzoic acid starting material with a conventional amino protecting group; (2) preparing the 1-benzotriazolyl active ester of the "blocked" amino-substituted benzoic acid; (d) reacting the active ester with the desired 7-(substituted)glycylaminocephalosporin substrate; and (4) deblocking the protected amino groups on the product cephalosporin compounds.

It is not necessary to block the phenolic hydroxy groups on the benzoic acid starting materials when the preparative procedure described hereinabove is employed for the preparation of the compounds of the present invention.

The compounds of the present invention can also be prepared by the alternate route depicted generally by the following reaction scheme.

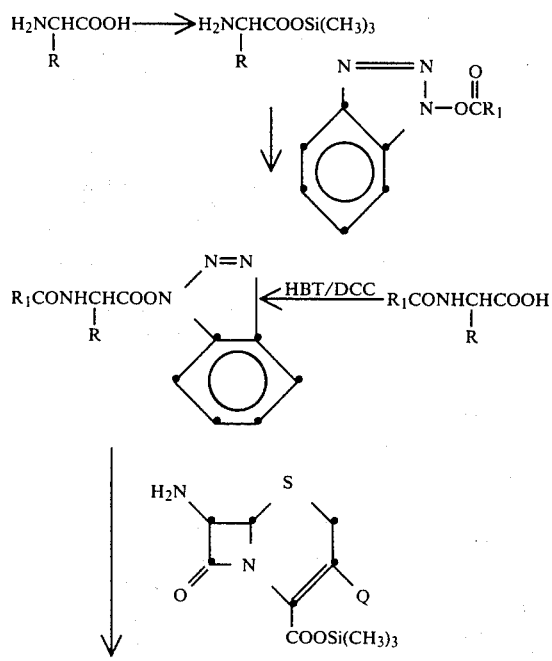

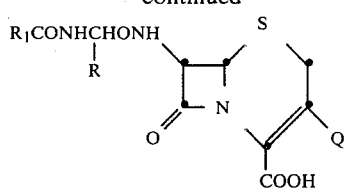

Essentially the same general reaction conditions described hereabove are applicable to the analogous steps, for example, silyl ester formation, active ester formation and acylation with active esters, in the depicted alternate preparation.

Although the foregoing discussion has been limited to the use of 1-hydroxybenzotriazole active esters, other conventional active esters including trichlorophenyl, pentachlorophenyl, 3,4-dihydro-4-oxo-1,2,3-benzotriazin-3-yl (U.S. Pat. No. 3,795,666) and substituted benzotriazolyl (U.S. Pat. No. 3,725,380) are suitable for the preparation of the present compounds.

Where the products of the foregoing preparative scheme are cephalosporins of the formula

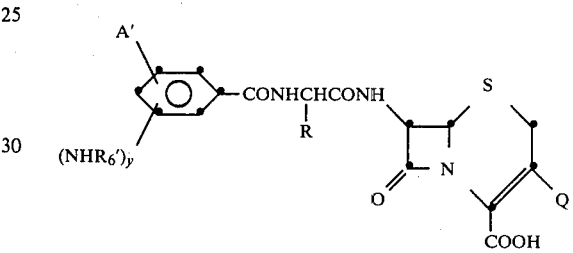

an additional deblocking step (removal of $R_6'$) is required to provide claimed biologically active compounds of this invention.

Illustrative of the cephalosporin antibiotics of the present invention of the formula

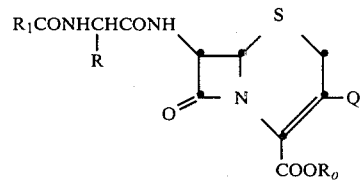

wherein $R_o$ is hydrogen are the following compounds represented in tabular form.

| R | $R_1$ | Q |
|---|---|---|
| phenyl | 2,3-dihydroxyphenyl | 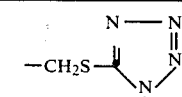 |
| 4-hydroxyphenyl | " | " |
| 3-chloro-4-hydroxyphenyl | " | " |
| 1,4-cyclohexadienyl | " | " |
| 2-thienyl | " | " |
| 2-furyl | " | " |
| 3-methansulfonamido phenyl | " | " |
| 3,4-dihydroxyphenyl | " | " |
| " | 3,4-dihydroxyphenyl | " |
| phenyl | " | " |

-continued

| R | R₁ | Q |
|---|---|---|
| 4-hydroxyphenyl | " | " |
| 1,4-cyclohexadienyl | " | " |
| 2-thienyl | " | " |
| phenyl | 3,4,5-trihydroxyphenyl | " |
| 4-hydroxyphenyl | " | " |
| 3-thienyl | " | " |
| 2-chlorophenyl | " | " |
| 1,4-cyclohexadienyl | " | " |
| 3-furyl | " | " |
| 4-benzyloxyphenyl | " | " |
| 2-methoxyphenyl | " | " |
| 3-nitrophenyl | " | " |
| phenyl | 2,3,4-trihydroxyphenyl | " |
| 4-hydroxyphenyl | " | " |
| 3-bromo-4-hydroxy-phenyl | " | " |
| 2-thienyl | 2-hydroxyphenyl | " |
| phenyl | " | " |
| " | 3-hydroxyphenyl | " |
| " | 2-amino-3-hydroxyphenyl | " |
| " | 2-hydroxy-3-aminophenyl | " |
| 4-hydroxyphenyl | 2,3-diaminophenyl | " |
| " | 3,4-diaminophenyl | " |
| " | 2-chloro-3,4-dihydroxy-phenyl | " |
| 2-thienyl | 3-methoxy-4-aminophenyl | " |
| phenyl | 3-hydroxyphenyl | —CH₂S—⟨N=N triazole-S, CH₃⟩ 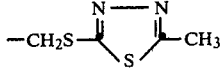 |
| " | 3-aminophenyl | " |
| " | 2,3-dihydroxyphenyl | " |
| 4-chlorophenyl | " | " |
| 4-hydroxyphenyl | " | " |
| 3,4-dihydroxyphenyl | " | " |
| 2-thienyl | 3,4-dihydroxyphenyl | " |
| 1,4-cyclohexadienyl | " | " |
| phenyl | " | " |
| 3-nitrophenyl | " | " |
| 3-chloro-4-methoxy-phenyl | " | " |
| phenyl | 3,4,5-trihydroxyphenyl | " |
| 4-hydroxyphenyl | " | " |
| 3-benzyloxyphenyl | " | " |
| 2-thienyl | " | " |
| 2-furyl | " | " |
| phenyl | 3-bromo-4-aminophenyl | " |
| phenyl | 2,3-dihydroxyphenyl | —CH₂S—⟨N=N, S, =O⟩ 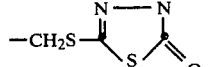 |
| 2-thienyl | 3,4-dihydroxyphenyl | " |
| 4-hydroxyphenyl | " | " |
| phenyl | 3,4,5-trihydroxyphenyl | —CH₂S—⟨N=N oxadiazole, CH₃⟩ 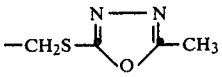 |
| phenyl | 3-amino-3,4-dihydroxy-phenyl | " |
| " | 2-chloro-3-hydroxyphenyl | acetoxymethyl |
| " | 3,4-dihydroxyphenyl | " |
| 4-hydroxyphenyl | " | " |
| 2-thienyl | " | " |
| phenyl | 3,4,5-trihydroxyphenyl | " |
| " | 2-hydroxy-3,5-diamino-phenyl | " |
| " | 2,5-dihydroxyphenyl | " |
| 4-hydroxyphenyl | 2,3-dihydroxyphenyl | methyl |
| phenyl | 3,4-dihydroxyphenyl | " |
| " | 3,4,5-trihydroxyphenyl | " |
| " | 3,5-dihydroxyphenyl | " |
| phenyl | 3,4-dihydroxyphenyl | —CH₂S—⟨N=N, N-CH₃ triazole⟩ 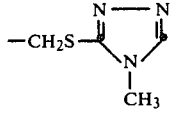 |
| 4-hydroxyphenyl | 2,3-dihydroxyphenyl | " |
| 1,4-cyclohexadienyl | " | " |
| 3-methanesulfon-amidophenyl | 3,4,5-trihydroxyphenyl | " |

-continued

| R | R₁ | Q |
|---|---|---|
| " | " | ![triazole structure] —CH₂S— with N=N ring, N-CH₃, CH₃ |
| " | 2-amino-3-hydroxyphenyl | " |
| " | 3,4-diaminophenyl | " |
| " | 4-hydroxyphenyl | —CH₂S— triazolone with N-CH₃, =O |
| 4-hydroxyphenyl | 2-chloro-3-aminophenyl | " |
| 2-furyl | 2,6-dihydroxyphenyl | " |
| 2-thienyl | 3,4,5-trihydroxyphenyl | " |
| 3-chloro-4-methoxy | 3-amino-2-hydroxyphenyl | —CH₂S— triazolethione with N-CH₃, =S |
| 4-trifluoromethyl-phenyl | 4-hydroxyphenyl | " |
| 4-hydroxyphenyl | 2,3-dihydroxyphenyl | " |
| 2-thienyl | 3,4,5-triaminophenyl | —CH₂S— triazole N-H |
| phenyl | 2-chloro-3,4,5-tri-hydroxyphenyl | " |
| 4-hydroxyphenyl | 3,4-dihydroxyphenyl | " |
| " | 2,3-dihydroxyphenyl | " |
| " | 3,4,5-trihydroxyphenyl | " |
| 2-furyl | 2-chloro-3,4-dihydroxy-phenyl | " |
| 3-chloro-4-hydroxy-phenyl | 2,3-dihydroxyphenyl | " |
| phenyl | 2,6-dihydroxyphenyl | —CH₂S— oxazole with CH₃, N, O |
| 1,4-cyclohexadienyl | 2,5-dihydroxyphenyl | " |
| 4-hydroxyphenyl | 2-amino-4-hydroxyphenyl | —CH₂S— thiazole N, S |
| phenyl | 2-hydroxyphenyl | —CH₂S— imidazole N-oxide |
| 2-thienyl | 3,4-dihydroxyphenyl | " |
| 2-furyl | 2-chloro-3-aminophenyl | " |
| 4-hydroxyphenyl | 3,4,5-trihydroxyphenyl | " |
| 3-methanesulfon-amidophenyl | 2,3-dihydroxyphenyl | " |
| phenyl | 2,3-dihydroxyphenyl | —CH₂S— triazinone with OH, =O, N-CH₃ |
| 3-methanesulfon-amidophenyl | 4-hydroxyphenyl | " |
| 4-hydroxyphenyl | 3,4-dihydroxyphenyl | " |
| " | 2,3-dihydroxyphenyl | " |
| " | 3,4,5-trihydroxyphenyl | " |
| 1,4-cyclohexadienyl | 3,4,5-trihydroxyphenyl | " |
| 2-thienyl | 2-amino-3-hydroxyphenyl | " |
| 2-furyl | 4-amino-3,4-dihydroxy-phenyl | " |
| 3-chloro-4-hydroxy- | 4-chloro-hydroxyphenyl | " |

| R | R₁ | Q |
|---|---|---|
| phenyl | | |
| 3-nitro-4-hydroxy-phenyl | 2-methyl-3,4-dihydroxy-phenyl | " |
| 4-benzyloxyphenyl | 3,4-diaminophenyl | " |
| 2-methyl-4-hydroxy-phenyl | 3-hydroxyphenyl | " |
| phenyl | 3,4-dihydroxyphenyl | chloro |
| " | 2,3-dihydroxyphenyl | " |
| 4-hydroxyphenyl | 3,5-dihydroxyphenyl | " |
| 3-hydroxyphenyl | 2-hydroxy-6-amino-phenyl | " |
| 1,4-cyclohexadienyl | 2,3-dihydroxyphenyl | " |
| 3-methanesulfon-amidophenyl | " | methoxymethyl |
| 1,4-cyclohexadienyl | 3,4-dihydroxyphenyl | " |
| 4-hydroxyphenyl | 3,4,5-trihydroxyphenyl | " |
| " | " | carbamoyloxymethyl |
| " | 2,3-dihydroxyphenyl | " |
| " | 3,4-dihydroxyphenyl | " |
| phenyl | 3,4-dihydroxyphenyl | N-methylcarbamoyl-oxymethyl |
| 2-thienyl | " | " |
| 2-furyl | 2,3-diaminophenyl | " |
| 2-chloro-4-hydroxy-phenyl | 3-amino-4,5-dihydroxy-phenyl | " |
| phenyl | 3,4,5,6-tetrahydroxy-phenyl | pyridiniummethyl |
| " | 2-hydroxyphenyl | " |
| " | 2-chloro-4-hydroxyphenyl | " |
| 4-hydroxyphenyl | 2,3-dihydroxyphenyl | " |
| phenyl | 2,3-diaminophenyl | 4-hydroxymethyl-pyridiniummethyl |
| " | 3,4-dihydroxyphenyl | " |
| 4-hydroxyphenyl | 2,6-dihydroxyphenyl | 3-carbamoylpyri-diniummethyl |
| 1,4-cyclohexadienyl | 3-amino-4-hydroxyphenyl | " |
| 2-thienyl | 2,3-dihydroxyphenyl | 3-acetylpyridinium-methyl |
| " | 3,4-dihydroxyphenyl | " |
| " | 2-chloro-3,4-dihydroxy-phenyl | " |
| 4-hydroxyphenyl | 2,3-dihydroxyphenyl | 4-carbamoyl-pyridiniummethyl |
| " | 3,4-dihydroxyphenyl | " |
| " | 3,4,5-trihydroxyphenyl | " |
| phenyl | " | " |
| " | 2,3-dihydroxyphenyl | " |
| " | 3,4-dihydroxyphenyl | " |

The antibiotic cephalosporin carboxylic acid ($R_o$=H) of the present invention are converted to the acyloxymethyl esters wherein in the above formula $R_o$ is represented by the group

by reacting an alkali metal salt of the cephalosporin carboxylic acid, for example, the sodium, potassium or lithium salt, with an acyloxymethyl halide of the formula

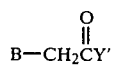

wherein B is chloro or bromo and Y' has the meanings assigned hereinabove. Acyloxymethyl halides which can be employed include chloromethyl acetate, bromomethyl acetate, bromomethyl propionate, chloromethyl pivaloate and benzoyloxymethyl chloride.

The preparation of the acyloxymethyl esters of the present invention is carried out by reacting the alkali metal salt form of the parent acid in an inert solvent with a slight molar excess of the bromo or chloromethyl ester, e.g., bromomethyl acetate at room temperature or at slightly elevated temperatures up to about 40°–45° C. Solvents such as acetone, tetrahydrofuran, dioxane, dimethylformamide, and methylene chloride can be used.

The indanyl esters of the present invention wherein $R_o$ is

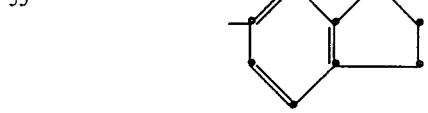

are prepared by reacting 5-indanol in an inert solvent such as dioxane or tetrahydrofuran with the free acid form of a compound of the present invention wherein in the above formula $R_o$ is hydrogen, in the presence of a condensing agent such as a diimide, for example, dicyclohexylcarbodiimide. The reaction is carried out with stirring at about 20°–35° C. for about 6 to 8 hours. The indanyl ester is isolated by first diluting the reaction mixture with water and filtering the reaction mixture to remove the insoluble dicyclohexylurea. The ester is then extracted from the filtrate.

Alternatively, the indanyl esters can be prepared by reacting a mixed acid anhydride formed with a cephalosporin acid of this invention and acetic acid with 5-indanol.

The phthalidyl esters of the formula I wherein $R_3$ is the phthalidyl group

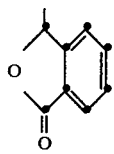

are obtained by reacting bromophthalide of the formula

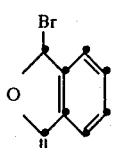

with a salt of a cephalosporin acid of the formula I. The esterification can be carried out in dimethylformamide, dimethylacetamide, dioxane, tetrahydrofuran, or mixtures thereof by slowly warming a mixture of equimolar amounts of the cephalosporin acid salt, for example, the sodium or potassium salt and bromophthalide.

The cephalosporin carboxylic acid compounds of this invention ($R_o=H$) form pharmaceutically acceptable salts with inorganic bases such as the alkali metal carbonates and bicarbonates. For example, the sodium and potassium salts can be formed with sodium and potassium carbonate respectively by following conventional procedures. Alternatively the cephalosporin free acid can be treated with sodium 2-ethylhexanoate in isopropanol to provide the corresponding sodium salt.

Salts can also be prepared with basic organic amines, such as methylamine, diethylamine, cyclohexylamine, dicyclohexylamine, ethanol amine, diethanol amine and tris-(hydroxymethyl)aminomethane.

Such salts can be used to formulate the antibiotics into suitable pharmaceutical forms for parental administration.

The cephalosporin antibiotics of this invention are highly effective in inhibiting the growth of a wide spectrum of pathogenic microorganisms of both the gram-positive and gram-negative type. Although the instant compounds exhibit high levels of activity against many gram-negative organisms, of special significance is the enhanced activity exhibited against the Pseudomonas gram-negative microorganisms. The antibiotic activity of the cephalosporin compounds of the present invention is illustrated by the data presented in Table I for representative compounds. The values in the table are the minimum inhibitory concentrations (MIC) for the test compounds against the indicated microorganisms. The MIC values were obtained in the Gradient Plate in vitro method for determining antibiotic activity.

TABLE I
ANTIBIOTIC ACTIVITY OF 7-[2-[(SUBSTITUTED BENZOYL)AMINO]ACETAMIDO]CEPHALOSPORINS
Minimum Inhibitory Concentration (mcg./ml.)

| Test Organism[1] | Test Compound[2] | | | | | | | | | | | |
|---|---|---|---|---|---|---|---|---|---|---|---|---|
| | A | B | C | D | E | F | G | H | I | J | K | L |
| Shigella sp. | 3.7 | 1.0 | 7.0 | 33 | 48 | 5.8 | 50 | 100 | 8.0 | 10.4 | 9.6 | 13.9 |
| Escherichia coli | 14.8 | 8.5 | 13.2 | 60 | 96 | 21.7 | 100 | 120 | 22.5 | 28.8 | 11.2 | 50 |
| Klebsiella pneumoniae | 10.0 | 0.8 | 4.1 | 29 | 29.5 | 3.9 | 52.5 | 110 | 3.9 | 16.8 | 8.9 | 29.5 |
| Aerobacter Aerogenes | 5.4 | 4.0 | 6.6 | 49 | 110 | 8.4 | 57.5 | 140 | 11 | 65.5 | 36.8 | 40 |
| Salmonella heidelberg | 0.5 | 0.2 | 1.0 | 32.5 | 82 | 0.7 | 16 | 110 | 1.0 | 26 | 25 | 33 |
| Pseudomonas Aeruginosa | 13.8 | 4.9 | 5.3 | 104 | 27.5 | 6.0 | 25 | 100 | 124 | >200 | 124 | >200 |
| Serratia marcescens | 16.4 | >200 | 80 | >200 | >200 | >200 | >200 | >200 | >200 | >200 | 80 | >200 |
| V41 | 15.1 | 3.6 | 23 | 4.6 | 3.7 | 6.6 | 60 | 10.5 | 16.2 | 1.0 | 1.0 | 1.0 |
| V32 | 132 | 3.8 | 23 | 4.0 | 4.6 | 8.6 | 60 | 10 | 14 | 1.0 | 1.1 | 1.0 |
| X466 | 136 | 8.4 | 130 | 41 | 60 | 130 | >200 | 120 | >200 | 92 | 122 | 84 |
| V84 | 10.3 | 3.2 | 22 | 2.2 | 1.3 | 3.2 | 25 | 10 | 11.6 | 1.0 | 1.0 | 1.0 |
| | M | N | O | P | Q | R | S | T | | | | |
| Shigella sp. | 13.8 | 5.7 | 26.5 | 9.8 | 9.2 | 18.0 | 50 | 58 | | | | |
| Escherichia coli | 19.0 | 10.1 | 28.0 | 16.5 | 18.0 | 82.0 | >200 | 74 | | | | |
| Klebsiella pneumoniae | 14.8 | 5.0 | 32.2 | 17.4 | 15.5 | 7.0 | 7.4 | 6.5 | | | | |
| Aerobacter Aerogenes | 33.2 | 9.1 | 43.5 | 22 | 36.0 | 50.0 | >200 | 76 | | | | |
| Salmonella heidelberg | 14.6 | 3.0 | 17.8 | 8.1 | 14.0 | 1.0 | 1.0 | 1.0 | | | | |
| Pseudomonas Aeruginosa | 31.5 | 92.0 | >200 | >200 | 92 | >200 | 56.0 | 140 | | | | |
| Serratia marcescens | 116 | >200 | >200 | >200 | >200 | >200 | >200 | >200 | | | | |
| V41 | 4.6 | 7.2 | 15.0 | 4.5 | 4.0 | 24 | 17.0 | 7.9 | | | | |
| V32 | 5.2 | 7.1 | 13.0 | 1.9 | 3.5 | 21.5 | 16.2 | 7.4 | | | | |
| X466 | 126 | 134.0 | >200 | 112 | 102 | >200 | >200 | >200 | | | | |
| V84 | 5.0 | 6.2 | 10.0 | 2.7 | 2.4 | 14.2 | 14.7 | 6.1 | | | | |

[1]Test organisms V41, V32, and V84 are penicillin resistant Staphylococcus. X400 is a methicillin resistant Staphylococcus.
[2]Test Compounds:

A. 7-[D-[2-Phenyl-2-[(2,3-dihydroxybenzoyl)amino]acetyl]amino]-3-[[(1-methyltetrazol-5-yl)thio]methyl]-3-cephem-4-carboxylic acid.

B. 7-[D-[2-(4-Hydroxyphenyl)-2-[(3,4-dihydroxybenzoyl)amino]acetyl]amino]-3-[[(1-methyltetrazol-5-yl)thio]methyl]-3-cephem-4-carboxylic acid.

C. 7-[D-[2-(4-Hydroxyphenyl)-2-[(2,3-dihydroxybenzoyl)amino]acetyl]amino]-3-[[(1-methyltetrazol-5-yl)thio]methyl]-3-cephem-4-carboxylic acid.

D. 7-[D-[2-(4-Hydroxyphenyl)-2-[(2-hydroxybenzoyl)amino]acetyl]amino]-3-[[(1-methyltetrazol-5-yl)thio]methyl]-3-cephem-4-carboxylic acid.

E. 7-[D-[2-(4-Hydroxyphenyl)-2-[(2,6-dihydroxybenzoyl)-amino]acetyl]amino]-3-[[(5-methyl-1,3,4-thiadiazol-2-yl)thio]methyl]-3-cephem-4-carboxylic acid.

F. 7-[D-[2-(4-Hydroxyphenyl)-2-[(3,4,5-trihydroxybenzoyl)-amino]acetyl]amino]-3-[[(5-methyl-1,3,4-thiadiazol-2-yl)thio]methyl]-3-cephem-4-carboxylic acid.

G. 7-[D-[2-(4-Hydroxyphenyl)-2-[(2,3,4-trihydroxybenzoyl)-amino]-acetyl]amino]-3-[[(5-methyl-1,3,4-thiadiazol-2-yl)thio]methyl]-3-cephem-4-carboxylic acid.

H. 7-[D-[2-(4-Hydroxyphenyl)-2-[(2,4,6-trihydroxybenzoyl)-amino]acetyl]amino]-3-[[(5-methyl-1,3,4-thiadiazol-2-yl)thio]methyl]-3-cephem-4-carboxylic acid.

I. 7-[D-[2-(4-Hydroxyphenyl)-2-[(2,3-dihydroxybenzoyl)-amino]acetyl]amino]-3-[[(4,5-dihydro-6-hydroxy-4-methyl-5-oxo-1,2,4-triazin-3-yl)thio]methyl]-3-cephem-4-carboxylic acid.

J. 7-[D-[2-(4-Hydroxyphenyl)-2-[(3-hydroxybenzoyl)amino]-acetyl]amino]-3-[[(5-methyl-1,3,4-thiadiazol-2-yl)thio]-methyl]-3-cephem-4-carboxylic acid.

K. 7-[D-[2-(4-Hydroxyphenyl)-2-[(3-chloro-4-hydroxybenzoyl)-amino]acetyl]amino]-3-[[(5-methyl-1,3,4-thiadiazol-2-yl)-thio]methyl]-3-cephem-4-carboxylic acid.

L. 7-[D-[2-(4-Hydroxyphenyl)-2-[(4-hydroxybenzoyl)amino]-acetyl]amino]-3-[[(5-methyl-1,3,4-thiadiazol-2-yl)-thio]methyl]-3-cephem-4-carboxylic acid.

M. 7-[D-[2-(4-Hydroxyphenyl)-2-[(3,4-diaminobenzoyl)amino]-acetyl]amino]-3-[[(5-methyl-1,3,4-thiadiazol-2-yl)-thio]methyl]-3-cephem-4-carboxylic acid.

N. 7-[D-[2-(4-Hydroxyphenyl)-2-[(2,3,4,5-tetrahydroxybenzoyl)amino]acetyl]amino]-3-[[(1-methyl-1,3,4-thiadiazol-2-yl)thio]methyl]-3-cephem-4-carboxylic acid.

O. 7-[D-[2-(4-Hydroxyphenyl)-2-[(2,5-dihydroxybenzoyl)-amino]acetyl]amino]-3-[[(1-methyltetrazol-5-yl)thio]-methyl]-3-cephem-4-carboxylic acid.

P. 7-[D-[2-(4-Hydroxyphenyl)-2-[(3,5-dihydroxybenzoyl)-amino]acetyl]amino]-3-[[(1-methyltetrazol-5-yl)thio]-methyl]-3-cephem-4-carboxylic acid.

Q. 7-[D-[2-(4-Hydroxyphenyl)-2-[(2,4-dihydroxybenzoyl)-amino]-acetyl]amino]-3-[[(1-methyltetrazol-5-yl)thio]-methyl]-3-cephem-4-carboxylic acid.

R. 7-[D-[2-Phenyl-2-[(2,3-dihydroxybenzoyl)amino]acetyl]-amino]-3-chloro-3-cephem-4-carboxylic acid.

S. 7-[D-[2-Phenyl-2-[(2,3-dihydroxybenzoyl)amino]acetyl]-amino]-3-acetoxymethyl-3-cephem-4-carboxylic acid.

T. 7-[D-[2-Phenyl-2-[(2,3-dihydroxybenzoyl)amino]acetyl]-amino]-3-carbamoyloxymethyl-3-cephem-4-carboxylic acid.

The novel cephalosporin carboxylic acids of the present invention, and the pharmaceutically acceptable salts thereof are useful in combating infections in warm-blooded mammals when administered parenterally in non-toxic doses between about 10 and 500 mg./kg. of body weight. The indanyl, phthalidyl and acyloxymethyl esters of this invention are useful antibiotics when administered orally in non-toxic doses of between 50 and 750 mg./kg. of body weight.

A preferred group of cephalosporins of this invention is the group represented by the generic formula

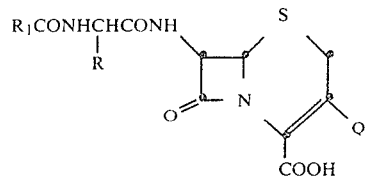

defining the compounds of the present invention wherein R is phenyl, 3-hydroxyphenyl, 4-hydroxyphenyl, 3-methane-sulfonamidophenyl, 2-thienyl or 1,4-cyclohexadienyl. More preferred are those compounds wherein R is phenyl or 4-hydroxyphenyl.

A further preferred group of cephalosporins of this invention is the group represented by the foregoing generic formula wherein $R_1$ is a group of the formula

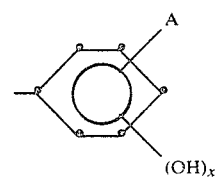

wherein A is hydrogen. More preferred are those cephalosporins of this invention wherein $R_1$ is a group of the formula

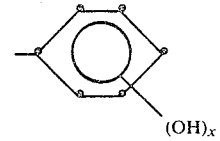

wherein X is 2 or 3 and wherein at least two of the hydroxy substituents are bonded to the phenyl ring at adjacent carbon atoms. A most preferred group of compounds of the present invention are those cephalosporins bearing a 2,3-dihydroxyphenyl, a 3,4-dihydroxyphenyl or a 3,4,5-trihydroxyphenyl group in the position of $R_1$ in the above generic formula.

Another preferred group of cephalosporins of this invention are those wherein the substituents represented by Q in the foregoing generic formula are substituents represented by the formula —$CH_2R_2$ wherein $R_2$ is as defined hereinabove. Preferred groups represented by $R_2$ are acetoxy, carbamoyloxy, methoxy, chloro, pyridinium or a group of the formula —$SR_3$ wherein $R_3$ is as defined hereinabove. More preferred of the groups representing $R_2$ is the group —$SR_3$ wherein $R_3$ is as defined hereinabove. A most preferred group of cephalosporin compounds of this invention are those compounds depicted by the above generic formula wherein Q is a group of the formula —$CH_2SR_3$ wherein $R_3$ is

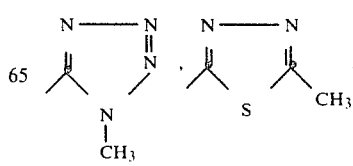

-continued

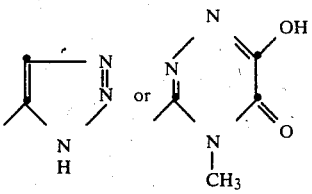

Accordingly most preferred compounds of the present invention are represented by the formula

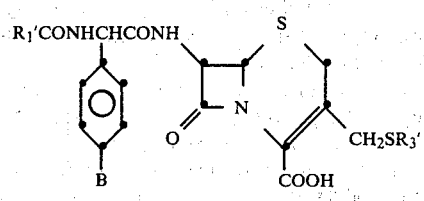

wherein B is hydrogen or hydroxy;

$R_1'$ is 2,3-dihydroxyphenyl, 3,4-dihydroxyphenyl or 3,4,5-trihydroxyphenyl; and $R_3'$ is a heteroaryl group selected from

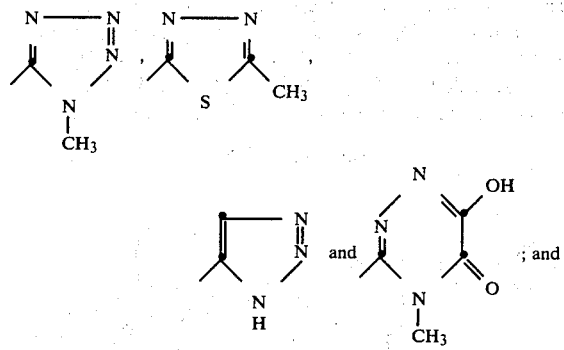

the pharmaceutically acceptable, non-toxic salts thereof.

The following examples are provided to further describe the invention and are not to be construed as limiting thereof.

EXAMPLE 1

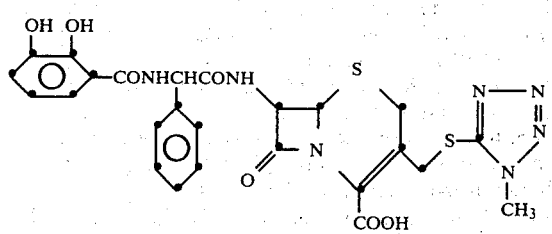

7-[D-[2-Phenyl-2-[(2,3-dihydroxybenzoyl-)amino]acetyl]amino]-3-[[(1-methyltetrazol-5-yl)thio]-methyl]-3-cephem-4-carboxylic acid.

To a solution of 308 mg. (2 mmol) of 2,3-dihydroxybenzoic acid and 306 mg. (2 mmol) of 1-hydroxybenzotriazole hydrate (HBT) in 4 ml. of dry tetrahydrofuran (THF) under nitrogen at 0° C. (ice bath) was added dropwise a solution of 494 mg. (2.4 mmol) of dicyclohexylcarbodiimide (DCC) in 2 ml. of dry THF. The ice bath was removed, and the reaction was stirred for 2 hours and then filtered to remove the dicyclohexylurea (DCU) precipitate. To the resulting cooled THF solution of the HBT active ester of 2,3-dihydroxybenzoic acid was added a cold solution of the silylated nucleus prepared as follows:

To 1.182 g. (2 mmol) of 7-[D-[(2-phenyl-2-amino)-acetyl]amino]-3-[[(1-methyltetrazol-5-yl)thio]methyl]-3-cephem-4-carboxylic acid, trifluoroacetic acid salt in 8 ml. of dry acetonitrile under nitrogen at 0° was added 2 ml. of bis(trimethylsilyl)acetamide. The reaction mixture was stirred until homogeneous and then evaporated in vacuo to dryness to provide the silylated nucleus. The aforementioned solution was prepared by dissolving the silylated nucleus in 2 ml. of cold THF.

After the cooled solutions of the silylated nucleus and the HBT active ester of 2,3-dihydroxybenzoic acid were combined, the reaction mixture was stirred at room temperature for 24 hours.

The reaction mixture was then evaporated in vacuo to dryness. Dry methanol was added to the residue and then was evaporated in vacuo to dryness. Ethyl acetate and water were added to the residue. The pH of the aqueous layer was adjusted to 8.5 with saturated aqueous sodium bicarbonate solution. The aqueous layer was then separated and layered with ethyl acetate while the pH was adjusted back to about 2.5. The organic layer was then separated, washed with brine and then dried by filtration through anhydrous sodium sulfate. Evaporation in vacuo to dryness provided an off white amorphous solid which was triturated with chloroform, dried in vacuo and then slurried in diethyl ether. Filtration of the ether slurry provided 636.5 mg. (53%) of the title product: uv(MeOH): λmax 250 (ε=17,633), 280 (shoulder) and 310 (shoulder); titration (66% DMF-34% H₂O) pK$_a$=5.31, 8.73; ir (KBr) 1770 cm$^{-1}$ (β-lactam C=O); nmr (DMSO d-6) δ3.97 (s, 3H, N—CH₃), 4.4 (broad s, 2H, C₃'—H₂), 5.50 (d, J=6 Hz, 1H, C₆—H), 5.9 (overlapping signals, 2H, C₇—H and C$_α$-H), 7.4 (broad signal, 8H, ArH), and 9.05 (overlapping doublets, 2H, N<u>H</u>).

EXAMPLE 2

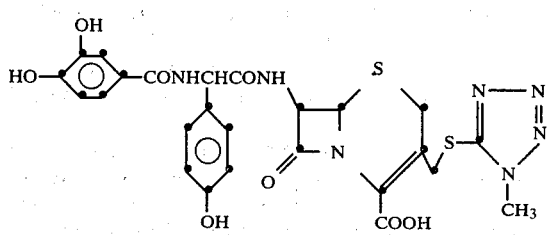

7-[D-[2-(4-hydroxyphenyl)-2-[(3,4-dihydroxybenzoyl-)amino]-acetyl]amino]-3-[[(1-methyltetrazol-5-yl)thio]-methyl]-3-cephem-4-carboxylic acid.

The title compound was prepared in accordance with the experimental procedure and on the same scale as described in Example 1. 3,4-Dihydroxybenzoic acid was substituted for the described 2,3-dihydroxybenzoic acid. A total of 274.1 mg. (22.4%) of the title product was isolated.

uv(MeOH): λmax 260 (ε=19,262), 285 mμ (shoulder); titration (66% DMF-34% H₂)) pK$_a$=4.10, 10.88; nmr (DMSO d-6) δ3.6 (broad, 2H, C₂—H), 3.95 (s, 3H, N—CH₃), 4.35 (broad, 2H, C₃'—H), 5.05 (d, J=5 Hz, 1H, C₆—H), 5.7 (overlapping signals, 2H, C₇—H and $C_\alpha$—H), 6.4–7.5 (overlapping signals, ArH) and 9.4 (overlapping signals).

EXAMPLE 3

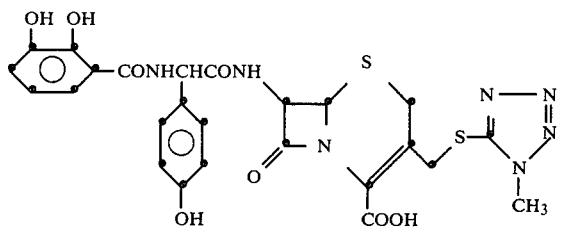

7-[D-[2-(4-Hydroxyphenyl)-2-[(2,3-dihydroxybenzoyl)amino]-acetyl]amino]-3-[[(1-methyltetrazol-5-yl)thio]-methyl]-3-cephem-4-carboxylic acid.

To a solution of 308 mg. (2 mmol) of 2,3-dihydroxybenzoic acid and 306 mg. (2 mmol) of 1-hydroxybenzotriazole hydrate (HBT) in 4 ml. of dry tetrahydrofuran under nitrogen at 0° C. (ice bath) was added dropwise a solution of 494 mg. (2.4 mmol) of dicyclohexylcarbodiimide (DCC) in 2 ml. of dry THF. The ice bath was removed, and the reaction was stirred for two hours and then filtered to remove the dicyclohexyl urea (DCU) precipitate. To the resulting cooled THF solution of the HBT active ester of 2,3-dihydroxybenzoic acid was added a cold solution of the silylated nucleus prepared as follows:

To 1.182 g. (2 mmol) of 7-[D-[[2-(4-hydroxyphenyl)-2-amino]acetyl]amino]-3-[[(1-methyltetrazole-5-yl)thio]-methyl]-3-cephem-4-carboxylic acid, trifluoroacetic acid salt in 8 ml. of dry acetonitrile under nitrogen at 0° was added 2 ml. of bis-(trimethylsilyl)-acetamide. The reaction mixture was stirred until homogeneous and then evaporated in vacuo to dryness to provide the silylated nucleus. The aforementioned solution was prepared by dissolving the silylated nucleus in about 2 ml. of cold THF.

After the cooled solutions of the silylated nucleus and the HBT active ester of 2,3-dihydroxybenzoic acid were combined, the reaction mixture was stirred at room temperature for 24 hours.

The reaction mixture was then evaporated in vacuo to dryness. Dry methanol was added to the residue and then was evaporated in vacuo to dryness. The residue thereby obtained was triturated with ethyl acetate. At this point the unreacted nucleus trifluoroacetic acid salt starting material was filtered from the ethyl acetate solution. The filtrate was then evaporated in vacuo to dryness and the resulting residue was triturated successively with diethyl ether and methylene chloride to provide 360 mg. of the title product as a cream-colored amorphous solid.

uv(MeOH) shoulders at 310, 280, and 245 mμ; titration (66% DMF-34% H$_2$O) pK$_a$=5.02, 8.83; nmr (DMSO d-6) δ3.62 (broad signal, 2H, C$_2$—H), 3.92 (s, 3H, N—CH$_3$), 4.25 (broad, 2H), 5.05 (d, J=6 Hz, 1H, C$_6$—H), 6.70 (overlapping signals, 2H, C$_7$—H and C$_\alpha$—H), 7.1–8.1 (7H, ArH), 9.1 (d, J=7 Hz, 1H, NH) and 9.3 (d, J=8 Hz, 1H, NH).

Anal. Calcd for C$_{25}$H$_{23}$N$_7$O$_8$S$_2$: C, 48.93; H, 3.98; N, 15.98; S, 10.45; Found: C, 51.14; H, 4.42; N, 15.58; S, 7.49.

EXAMPLE 4

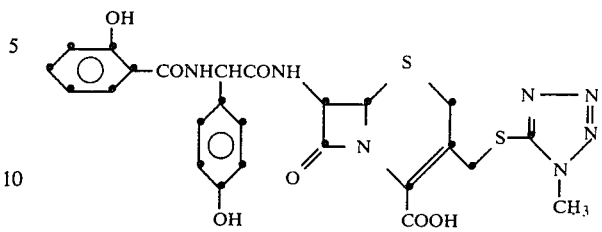

7-[D-[2-(4-Hydroxyphenyl)-2-[(2-hydroxybenzoyl)amino]acetyl]-amino]-3-[[(1-methyltetrazol-5-yl)-thio]-methyl]-3-cephen-4-carboxylic acid.

The title compound was prepared in accordance with the experimental procedure and on the same scale as described in Example 3. 2-Hydroxybenzoic acid was substituted for the described 2,3-dihydroxybenzoic acid. A total of 300 mg. of the title product was isolated [tlc (7:3-CHCl$_3$:MeOH) shows minor impurity-hydroxybenzotriazole-probably due to insufficient trituration with methylene chloride]: ir(mull) 1770 cm$^{-1}$ (β-lactam C=O); titration (66% DMF-34% H$_2$O) pK$_a$=5.09, 10.02; nmr (DMSO d-6) δ3.7 (broad, 2H, C$_2$—H), 4.0 (s, 3H, N—CH$_3$), 4.35 (broad, 2H, C$_3'$—H), 5.1 (d, J=5 Hz, 1H, C$_6$—H), 5.8 (overlapping signals, 2H, C$_7$—H and C$_\alpha$—H), 6.5–8.2 (ArH), 8.8 (NH), 9.55 (NH).

Anal Calcd for C$_{25}$H$_{23}$N$_7$O$_7$S$_2$: C, 50.24; H, 3.88; N, 16.41; Found: C, 49.61; H, 4,98; N, 17.11.

EXAMPLE 5

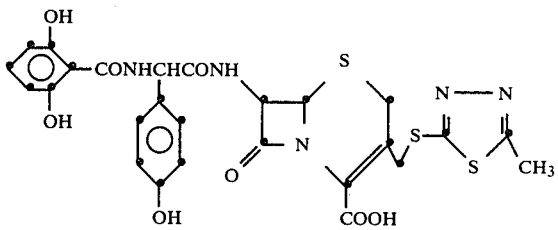

7-[D-[2-(4-Hydroxyphenyl)-2-[(2,6-dihydroxybenzoyl)amino-acetyl]amino]-3-[[(5-methyl-1,3,4-thiadiazol-2-yl)thio]-methyl]-3-cephem-4-carboxylic acid.

To a solution of 3.08 g. (20 mmol) of 2,6-dihydroxybenzoic acid and 3.06 g. of 1-hydroxybenzotriazole hydrate (HBT) in 40 ml. of dry THF under nitrogen at 0° (ice bath) was added dropwise a solution of 4.94 g. (20 mmol) of dicyclohexylcarbodiimide (DCC). The ice bath was removed and after stirring for two hours at room temperature, the reaction mixture was filtered to remove the dicylohexylurea (DCU) precipitate. A 4 ml. aliquot of the resulting THF solution of the HBT active ester of 2,6-hydroxybenzoic acid was combined with a cold solution of the silylated nucleus prepared as follows:

To 960 mg. (2 mmol) of 7-[D-[[2-(4-hydroxyphenyl)-2-amino]acetyl]amino]-3-[[(5-methyl-1,3,4-thiadiazol-2-yl)thio]methyl]-3-cephem-4-carboxylic acid, trifluoroacetic acid salt in 16 ml. of dry acetonitrile under nitrogen 0° was added 2 ml. of bis-(trimethylsilyl)-acetamide. The reaction mixture was stirred until homogeneous and then evaporated in vacuo to dryness to provide the silylated nucleus. The silylated nucleus was then dissolved in 2 ml. of dry THF.

After the cooled solutions of the silylated nucleus and the HBT active ester of 2,6-dihydroxybenzoic acid (4 ml. of above described solution) were combined, the reaction mixture was stirred overnight at room temperature.

The reaction mixture was then evaporated in vacuo to dryness. Dry methanol (2 ml.) was added to the residue and then was evaporated in vacuo. The residue was then triturated with ethyl acetate, and the resulting slurry was filtered. Evaporation in vacuo of the filtrate (ethyl acetate) provided a residue which was then triturated successively with diethyl ether and methylene chloride. A total of 450 mg. of the title product was obtained as a cream-colored amorphous solid which was shown to be pure by tlc (silica gel, 7:3 chloroform-methanol).

uv(MeOH) $\lambda$max 255 ($\epsilon$=23,333), shoulders at 280 and 315 m$\mu$; Tritration (66% DMF—34% H$_2$O) pK$_a$=5.20 , 9.13; ir (mull) 1770 cm$^{-1}$ ($\beta$-lactam C=O)

Anal. Calcd for C$_{26}$H$_{23}$N$_5$O$_8$S$_3$: C, 49.59; H, 3.68; N, 11.12. Found: C, 48.03; H, 3.99; N, 13.04.

After the cooled solutions of the silylated nucleus and the HBT active ester of 3,4,5-trihydroxybenzoic acid were combined, the reaction mixture was stirred at room temperature for 24 hours.

The reaction mixture was then evaporated in vacuo to dryness. Dry methanol was added to the residue and then was evaporated in vacuo. The residue thereby obtained was triturated with dilute HCl (pH=1.5) and then was washed successively with water and diethyl ether and then dried in a dessicator. A subsequent thorough trituration of the dried product with 150 ml. of dilute HCl (pH=1.5) followed by washings with water and ether provided 610 mg. (after drying) of the title product as a cream-colored amorphous solid. Thin-layer chromatography (silica gel, acetone-water-acetic acid, 100:10:1) showed only minor impurities.

ir (mull) 1700 cm$^{-1}$ ($\beta$-lactam C=O); uv(MeOH) $\lambda$max 272 m$\mu$ ($\epsilon$=21,000); Tritration (66% DMF-34% H$_2$O) pK$_a$=4.88, 1060.

Anal. Calcd for C$_{26}$N$_{23}$N$_5$O$_9$S$_3$: C, 48.36; H, 3.59 N, 10.85. Found: C, 48.01; H, 3.83; N, 10.50.

EXAMPLE 6

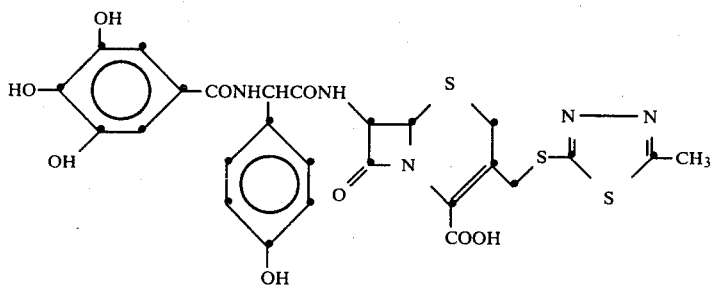

7-[D-[2-(4-hydroxyphenyl)-2-[(3,4,5-trihydroxybenzoyl)-amino]acetyl]amino]-3-[[(5-methyl-1,3,4-thiadiazol-2-yl)thio]methyl]-3-cephem-4-carboxylic acid.

To a solution of 376 mg. (2 mmol) of 3,4,5-trihydroxybenzoic acid and 306 mg. (2 mmol) of 1-hydroxybenzotriazole hydrate in 4 ml. of dry tetrahydrofuran under nitrogen at 0° C. (ice bath) was added dropwise a solution of 494 mg. (2.4 mmol) of dicyclohexylcarbodiimide in 2 ml. of dry THF. The ice bath was removed, and after stirring for two hours, the reaction mixture was filtered to remove the dicyclohexyl urea precipitate. The resulting THF solution of the HBT active ester of 3,4,5-trihydroxybenzoic acid was added to a cold solution of the silylated nucleus prepared from 960 mg. (2 mmol) of 7-[D-[[(2-(4-hydroxyphenyl)-2-amino]acetyl-]amino]-3-[[(5-methyl-1,3,4-thiadiazol-2-yl)thio]methyl]-3-cephem-4-carboxylic acid in accordance with the procedures described in Example 5.

EXAMPLE 7

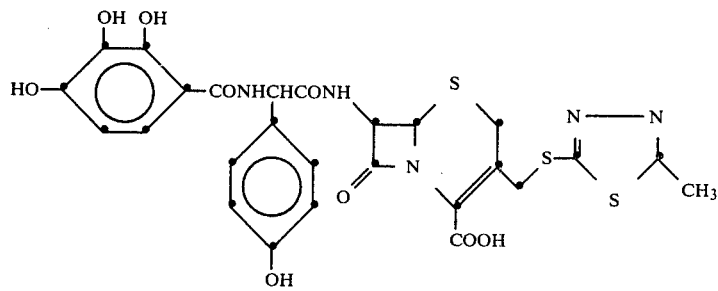

7-[D-[2-(4-Hydroxyphenyl)-2-[(2,3,4-trihydroxybenzoyl)-amino]acetyl]amino]-3-[[(5-methyl-1,3,4-thiadiazol-2-yl)thio]methyl]-3-cephem-4-carboxylic acid.

The title compound was prepared in accordance with the procedure described in Example 6; 2,3,4-trihydroxybenzoic acid was substituted for the 3,4,5-trihydroxybenzoic acid therein employed. Also several modifications in the product isolation steps were found necessary. Work-up in accordance with Example 6 gave 300 mg. of a light tan-colored powder-tlc (silica gel, acetone-water-acetic acid, 100:10:1) shows front-running impurity and some of the unreacted starting material. Purification was accomplished by trituration with 2-300 ml. portions of ethyl acetate which had been filtered through sodium bicarbonate. Evaporation in vacuo of the combined ethyl acetate extracts provided 90 mg. of the title product as an off-white amorphous powder.

ir (mull) 1770 cm$^{-1}$ ($\beta$-lactam C=O);
Anal. Calcd for C$_{26}$H$_{23}$N$_5$O$_9$S$_3$: C, 48.36; H, 3.59; N, 10.85. Found: C, 48.56; H, 3.81; N, 10.58.

EXAMPLE 8

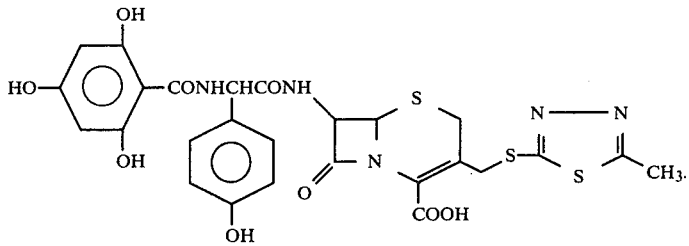

7-[D-[2-(4-Hydroxyphenyl)-2-[(2,4,6-trihydroxybenzoyl)-amino]acetyl]amino]-3-[[(5-methyl-1,3,4-thiadiazol-2-yl)-thio]methyl]-3-cephem-4-carboxylic acid.

The title compound was prepared and isolated in accordance with the procedure described in Example 6; 2,4,6-trihydroxybenzoic acid was substituted for the 3,4,5-trihydroxybenzoic acid, therein employed.

ir (mull) 1770 cm$^{-1}$ ($\beta$-lactam C=O)
Anal. Calcd. for C$_{26}$H$_{23}$N$_5$O$_9$S$_3$: C, 48.36; H, 3.59; N, 10.85. Found: C, 50.06; H, 4.63; N, 11.54.

EXAMPLE 9

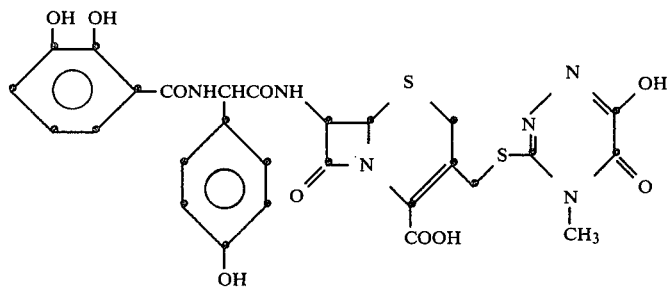

7-[D-[2-(4-Hydroxyphenyl)-2-[(2,3-dihydroxybenzoyl)amino]acetyl]amino]-3-[[(4,5-dihydro-6-hydroxy-4-methyl-5-oxo-1,2,4-triazin-3-yl)thio]methyl]-3-cephem-4-carboxylic acid.

The title compound was prepared and isolated in accordance with the procedure described in Example 3; 1.26 g. (2 mmol) of 7-[D-[[2-(4-hydroxyphenyl)-2-amino]-acetyl]amino-]3-[[(4,5-dihydro-6-hydroxy-4-methyl-5-oxo-1,2,4-triazin-3-yl)thio]methyl]-3-cephem-4-carboxylic acid, trifluoroacetic acid salt was substituted in the procedure for the corresponding "tetrazol-thio-nucleus" employed in Example 3. The title product was isolated as cream-colored amorphous solid (470 mg.).

uv (methanol) $\lambda$max shoulder 245, 280, 300 m$\mu$; Titration (66% DMF-34% H$_2$O) pK$_a$=4.99 and 8.89; ir (mull) 1770 cm$^{-1}$ ($\beta$-lactam C=O); nmr (DMSO d-6) $\delta$3.3 (s, 3H, CH$_3$), 3.6 (broad s, 2H, C$_2$—H), 5.1 (d, J=6, 1H, C$_6$—H), 5.6-6.0 (overlapping signals, 2H, C$_7$—H and C$_\alpha$—H), 6.6-7.6 (overlapping signals, 7H, ArH), 9.3 (overlapping signals, 3H), and 13.6 (broad s, NH).

EXAMPLE 10

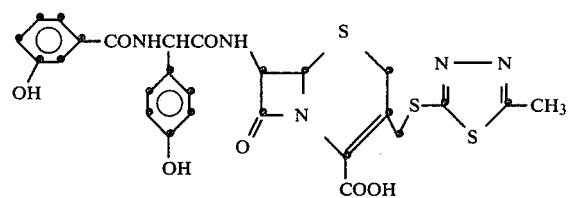

7-[D-[2-(4-Hydroxyphenyl)-2-[(3-hydroxybenzoyl)amino]acetyl]amino]-3-[[(5-methyl-1,3,4-thiadiazol-2-yl)thio]methyl]-3-cephem-4-carboxylic acid.

The title compound was prepared in accordance with the procedure described in Example 5; 3-hydroxybenzoic acid was substituted for the 2,6-dihydroxybenzoic acid therein employed. A standard aqueous acid/base extraction-isolation procedure provided 258 mg. (21%) of the title product as a light pink amorphous solid:

ir(mull) 1700 cm$^{-1}$ ($\beta$-lactam C=O); uv(methanol) $\lambda$max 272 ($\epsilon$=13,669); Titration (66% DMF-34% H$_2$O) pK$_a$=5.02, 11.92; nmr(DMSO d-6) $\delta$2.7 (s, 3H, CH$_3$), 3.6 (broad s, 2H, C$_2$—H), 4.35 (mult), 6.8 (d, J=8 Hz, 2H, ArH), 7.35 (overlapping signals, 6H, ArH), 8.45 (d, J=7 Hz 1H, —NH), and 9.1 (mult, 1H, —NH).

Anal. Calcd for C$_{26}$H$_{23}$N$_5$O$_7$S$_3$: C, 50.89; H, 3.78; N, 11,41; S, 15.67. Found: C, 49.84; H, 4.14; N, 12.34; S, 12.85.

EXAMPLE 11

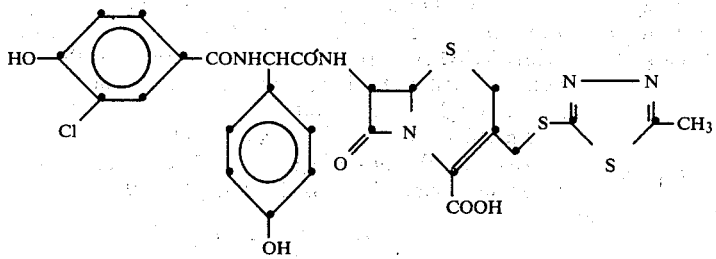

7-[D-[2-(4-Hydroxyphenyl)-2-[(3-chloro-4-hydroxybenzoyl)amino]acetyl]amino]-3-[[(5-methyl-1,3,4-thiadiazol-2-yl)thio]methyl]-3-cephem-4-carboxylic acid.

The title compound was prepared in accordance with the procedure described in Example 5; 3-chloro-4-hydroxybenzoic acid was substituted for the 2,6-dihydroxybenzoic acid therein employed. A standard acid/base extraction-isolation procedure provided 394 mg. (30%) of the title product as an off-white amorphous solid: ir(mull) 1770 cm$^{-1}$ ($\beta$-Lactam C=O); uv(methanol) $\lambda$max 259 ($\epsilon$=23,059); Titration (66% DMF-34% water) pK$_a$=4.9, 9.5; nmr(DMSO d-6) $\delta$2.7 (s, 3H, CH$_3$), 3.6 (broad s, 2H, C$_2$—H), 4.3 (broad, 2H, C$_3$—H), 5.1 (mult, 2H, C$_6$—H), 5.7 (overlapping signals, 2H, C$_7$—H and C$_\alpha$—H), 6.7–8.0 (mult, ArH), 8.5 (d, J=7 Hz, 1H, —NH) and 9.1 (mult, 1H, —NH).

Anal. Calcd for C$_{26}$H$_{22}$N$_5$O$_7$S$_3$Cl C, 48.18; H, 3.42; N, 10.81; S, 14.84; Cl, 5.47. Found: C, 47.47; H, 3.78; N, 12.20; S, 12.53; Cl, 5.01.

EXAMPLE 12

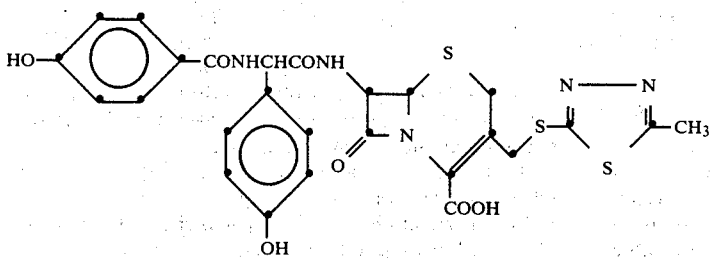

7-[D-[2-(4-Hydroxyphenyl)-2-[(4-hydroxybenzoyl)amino]acetyl]-amino]-3-[[(5-methyl-1,3,4-thiadiazol-2-yl)thio]methyl]-3-cephem-4-carboxylic acid.

The title compound was prepared in accordance with the procedure described in Example 5; 4-hydroxybenzoic acid was employed instead of 2,6-dihydroxybenzoic acid. The preparation was carried out on a 4 mmole scale. A standard acid/base aqueous isolation procedure provided 190 mg. (7.8%) of the title compound. The low yield indicates that the product is quite water soluble.

ir(mull) 1765 cm$^{-1}$ ($\beta$-lactam C=O); nmr(DMSO d-6) $\delta$2.7 (s, 3H, CH$_3$), 3.6 (broad s, 2H, C$_2$—H), 4.3 (broad, 2H, C$_3'$—H), 5.1 (mult, 1H, C$_6$—H), 5.8 (overlapping signals, 2H, C$_7$—H and C$_\alpha$—H), 6.6–8.0 (mult, ArH), 8.5 (1H, —NH), and 9.25 (1H, —NH).

Anal. Calcd for C$_{26}$H$_{23}$N$_5$O$_7$S$_3$: C, 50.89; H, 3.78; N, 11.41; S, 15.67. Found: C, 49.59; H, 4.02; N, 13.32; S, 12.08.

EXAMPLE 13

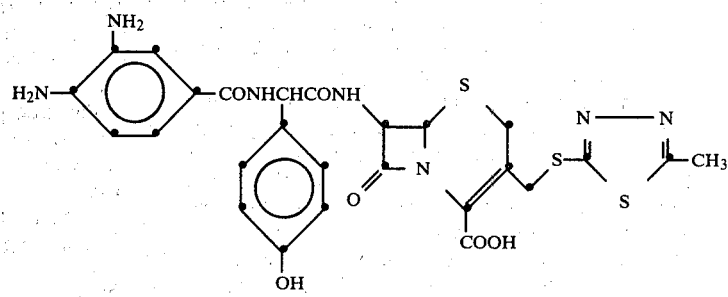

7-[D-[2-(4-Hydroxyphenyl)-2-[(3,4-diaminobenzoyl)amino]acetyl]amino]-3-[[(5-methyl-1,3,4-thiadiazol-2-yl)thio]methyl]-3-cephem-4-carboxylic acid.

A. Preparation of 3,4-di(tert-butoxycarbonylamino)benzoic acid

To a solution of 7.60 g. (50 mmol) of 3,4-diaminobenzoic acid and 27.8 ml. (200 mmol) of triethylamine in 150 ml. of water at room temperature was added dropwise a solution of 17.0 ml. (100 mmol) of tert-butoxycarbonylazide in 150 ml. of dioxane. The reaction mixture was allowed to stir overnight. The volume of the reaction mixture was then reduced in vacuo to approximately 50% of the original volume. The aqueous solution remaining was washed with diethyl ether and then layered with ethyl acetate. After cooling the mixture in an ice-water bath the pH of the aqueous layer was adjusted to 2.5 by the addition of cold 1 molar HCl. The ethyl acetate layer was then separated, washed with brine, and dried over anhydrous sodium sulfate. Evaporation in vacuo provided an oil which upon trituration with diethyl ether provided the title product as a gray solid.

B. Preparation of 7-[D-[2-(4-hydroxyphenyl)-2-[[3,4-di(tert-butoxycarbonylamino)benzoyl]amino]acetyl]-amino]-3-[[(5-methyl-1,3,4-thiadiazol-2-yl)thio]methyl]-3-cephem-4-carboxylic acid.

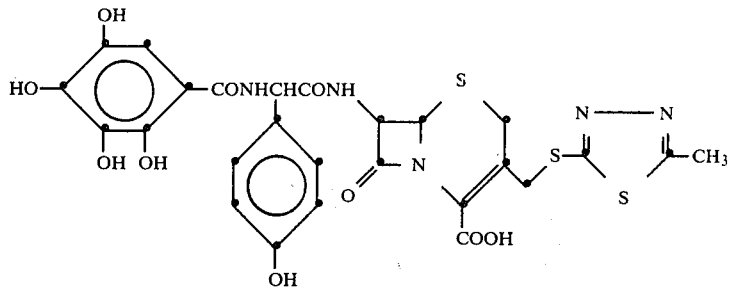

To a solution of 343 mg. (~1 mmol) of the unpurified product from paragraph A hereinabove and 153 mg. (1 mmol) of 1-hydroxybenzotriazole in 2 ml. of dry tetrahydrofuran at 0° was added a solution of 247 mg. of dicyclohexylcarbodiimide in 2 ml. of tetrahydrofuran. The mixture was allowed to stir at room temperature for about 2 hours. Filtration of the reaction mixture under nitrogen provided a THF solution of 1'-benzotriazolyl 3,4-di(tert-butoxycarbonylamino)benzoate which was then added to a solution of 1 mmol. of trimethylsilyl 7-[D-(2-(4-hydroxyphenyl)-2-aminoacetyl-]amino]-3-[[(5-methyl-1,3,4-thiadiazol-2-yl)-thio]methyl]-3-cephem-4-carboxylate (See Example 5 hereinabove) in 1 ml. of tetrahydrofuran. The reaction mixture was allowed to stir at room temperature for about 2 hours, after which time it was added to a mixture of water and ethyl acetate. The pH of the aqueous layer was adjusted to pH 7. The aqueous layer was then separated and layered with fresh ethyl acetate. After the pH of the aqueous layer was adjusted to 2.5 with dilute HCl, the ethyl acetate layer was separated and washed successively with dilute HCl (pH 2) and brine (2X), and then dried over anhydrous sodium sulfate. Evaporation in vacuo to dryness of the ethyl acetate solution provided a residue which was triturated with diethyl ether to provide 76 mg. of the titled protected amino benzoyl derivative.

C. Cleavage of the tert-butoxycarbonyl protecting groups.

The product from paragraph B above was added to 1 ml. of trifluoroacetic acid at 0° under a nitrogen atmosphere. The mixture was allowed to stir for 15 minutes at about 0° after which time the mixture was evaporated in vacuo to dryness. Twice methylene chloride was added to the mixture and evaporated in vacuo to dryness. Trituration of the residue thereby obtained with diethyl ether provided 65 mg. of a light brown solid. Comparative thin-layer chromatography (silica gel 7:3/CHCl$_3$—CH$_3$OH) showed clearly that cleavage of the protecting groups was not complete. The product, therefore, was again dissolved in 1 ml. of trifluoroacetic acid at 0° under nitrogen and allowed to stir for an additional 30 minutes, after which time the reaction mixture was evaporated in vacuo to dryness. Twice methylene chloride was added to the residue and evaporated to dryness. Trituration of the resulting residue with diethyl ether provided 48 mg. of the di-trifluoroacetic acid salt of the titled diaminobenzoylamino derivative as a light brown solid.

ir(mull) 1775 cm$^{-1}$ ($\beta$-lactam C=O).

Anal. Calcd. For C$_{30}$H$_{27}$N$_7$O$_{10}$S$_3$F$_6$ C, 42.11; H, 3.18; N, 11.46. Found: C, 43.32; H, 3.37; N, 11.96.

EXAMPLE 14

7-[D-[α-(4-Hydroxyphenyl)-2-[(2,3,4,5-tetrahydroxybenzoyl)-amino]acetyl]amino]-3-[[(1-methyl-1,3,4-thiadiazol-2-yl)-thio]methyl]-3-cephem-4-carboxylic acid.

The title product was prepared in accordance with the procedure described in Example 5; 2,3,4,5-tetrahydroxybenzoic acid was used instead of the 2,6-dihydroxy-benzoic acid employed therein. The product, after being twice triturated with dilute HCl, was isolated as a light brown amorphous solid (498 mg., 32%).

ir(mull) 1778 cm$^{-1}$ ($\beta$-lactam C=O); Titration (66% DMF-36% water) pK$_a$=4.98; 7.63, 9.69.

Anal. Calcd. for C$_{26}$H$_{23}$N$_5$O$_{10}$S$_3$ C, 47.20; H, 3.50; N, 10.58; S, 14.54. Found: C, 44.04; H, 3.77; N, 10.90; s, 13.77.

EXAMPLE 15

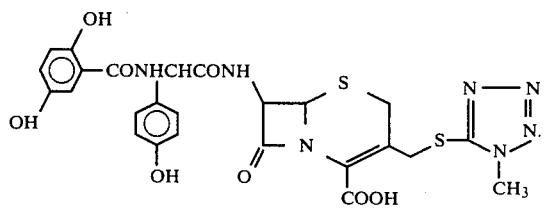

7-[D-[2-(4Hydroxyphenyl)-2-[(2,5-dihydroxybenzoyl)amino]-acetyl]amino]-3-[[(1-methyltetrazol-5-yl)thio]-methyl]-3-cephem-4-carboxylic acid.

The preparation of the title compound was carried out in accordance with the general procedures described in Example 1; 2,5-dihydroxybenzoic acid was substituted for 2,3-dihydroxybenzoic acid. After stirring the final acylation mixture for 24 hours, 5 ml. of methanol was added and the resulting solution was evaporated in vacuo to dryness. The residue was dissolved in ethyl acetate, and the resulting solution was washed successively with 0.1 N HCl (2X) and brine, and dried by filtering through anhydrous sodium sulfate. Evaporation in vacuo to dryness provided a residue which was washed with methylene chloride and then suspended in diethyl ether. Filtration provided 656.1 mg. of the product (contaminated with dicyclohexylurea—DCU) This impure product was dissolved in THF; the insoluble DCU was filtered, and the filtrate was evaporated in vacuo to dryness to give 559.5 mg. (45%) of the title product.

ir(mull) 1775 cm$^{-1}$ ($\beta$-lactam C=O); uv(methanol) $\lambda$max 320 ($\epsilon$=3,678); Titration (66% DMF-34% water) pK$_a$=5.08, 10.99, 12.5; nmr(DMSO d-6) $\delta$3.63 (broad, 2H, C$_3'$—H), 4.0 (s, 3H, CH$_3$), 4.32 (broad, 2H, C$_2$—H), 5.05 (d, 1H, J=5, C$_6$—H), 5.65 (mult, 2H, C$_7$—H and C$_\alpha$—H), and 6.7-7.6 (ArH).

EXAMPLE 16

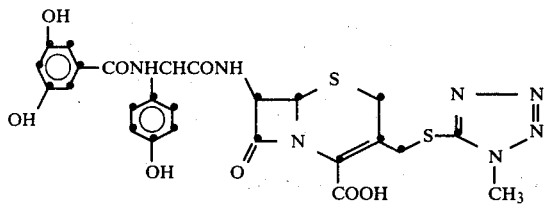

7-[D-[2-(4-Hydroxyphenyl)-2-[(3,5-dihydroxybenzoyl)amino]-acetyl]amino]-3-[[(1-dimethyltetrazol-5-yl)thio]methyl]-3-cephem-4-carboxylic acid.

The title compound was prepared in accordance with the procedures described in Example 1. Isolation and purification of the product by those procedures described in Example 15 provided 561.7 mg. (46%) of the title product (bioautogram showed some starting material present).

ir(KBr) 1770 cm$^{-1}$ ($\beta$-lactam C=O); uv(methanol) $\lambda$max 255 ($\epsilon$=13,200); Titration (66% DMF-34% water) pK$_a$=5.22, 11.73, $\geq$12; nmr (DMSO d-6) $\delta$3.6 (broad s, 2H, C$_2$—H), 3.95 (s, 3H, N—CH$_3$), 4.29 (broad s, 2H, C$_3'$—H), 5.03 (d, 1H, C$_6$—H), 5.4-5.7 (overlapping signals, 2H, C$_7$—H and C$_\alpha$—H) and 6.6-7.4 (mult, ArH).

EXAMPLE 17

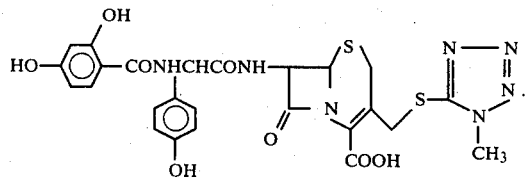

7-[D-[2-(4-Hydroxyphenyl)-2-[(2,4-dihydroxybenzoyl)amino]-acetyl]amino]-3-[[(1-methyltetrazol-5-yl)thio]methyl]-3-cephem-4-carboxylic acid.

The title compound was prepared by the same procedure described in Example 1; 2,4-dihydroxybenzoic acid was substituted for the 2,3-dihydroxybenozic acid employed therein. The crude product was isolated and purified by the particular procedures described in Example 15 to give 598.1 mg. (49%) of the title product (bioautogram show some starting material and DCU present).

ir(KBr) 1770 cm$^{-1}$ ($\beta$-lactam C=O); uv(methanol) $\lambda$max 260 ($\epsilon$=20,130); Titration (66% DMF-34% water) pK$_a$=4.97, 9.58, 12.14; nmr (DMSOd-6) $\delta$3.66 (broad s, 2H, C$_2$—H), 4.0 (s, 3H, N—CH$_3$), 4.28 (broad s, 2H, C$_3'$—H), 5.04 (d, 1H, J=5.0 Hz, C$_6$—H), 6.5-6.8 (overlapping signals, 2H, C$_7$—H and C$_\alpha$—H), and 6.3-7.4 (mult, ArH).

EXAMPLE 18

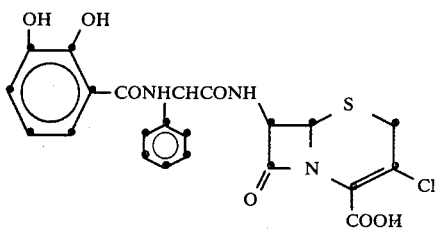

7-[D-[2-phenyl-2-[(2,3-dihydroxybenzoyl)amino]acetyl]amino]-3-chloro-3-cephem-4-carboxylic acid.

7-[D-[2-Phenyl-2-aminoacetyl]amino]-3-chloro-3-cephem-4-carboxylic acid (2 mmol) was first silylated and then acylated with 1-benzotriazolyl 2,3-dihydroxybenzoate in accordance with the general procedure described in Example 1. The title product was isolated and purified using the procedure described in Example 15 hereinabove. Yield-237 mg. (23%).

ir(KBr) 1775 cm$^{-1}$ ($\beta$-lactam C=O); uv(methanol) $\lambda$max 244 ($\epsilon$=13,929), 310 ($\epsilon$=~4000); Titration (66% DMF-34% water) pK$_a$=4.55, 3.84; nmr(DMSOd-6) $\delta$3.8 (Abq, 2H, C$_2$—H), 5.12 (d, J=4.5, 1H, C$_6$—H), 5.5-5.9 (mult, 2H, C$_7$—H and C$_\alpha$—H), 6.7-7.7 (ArH) and 9.5 (m, 2H, 2—NH).

EXAMPLE 19

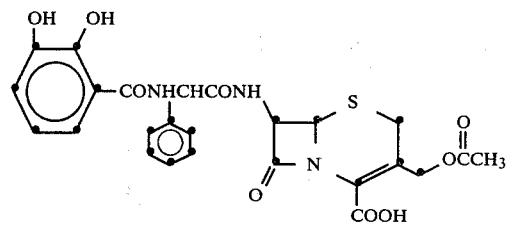

7-[D-[2-Phenyl-2-[(2,3-dihydroxybenzoyl)amino]acetyl]amino]-3-acetoxymethyl-3-cephem-4-carboxylic acid.

In accordance with the general procedures described in Example 1 cephaloglycine .2H$_2$O (2 mmol) was first silylated with excess bis-(trimethylsilyl)-acetamide (BSA) and then acylated with 1'-benzotriazolyl 2,3-dihydroxybenzoate (2 mmol). The title product was isolated in accordance with the isolation procedures described in Example 15. Yield-380 mg. (35%).

ir(KBr) 1770 cm$^{-1}$ ($\beta$-lactam C=O); uv (methanol) $\lambda$max 246 ($\epsilon$=15,086), 310 ($\epsilon$=~4300); Titration (66% DMF—34% water) pK$_a$=5.0, 8.72; nmr (DMSOd-6) $\delta$2.05

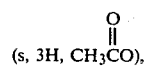

(s, 3H, CH$_3$CO), 3.52 (ABq, 2H, C$_3'$—H), (broad s, 2H, C$_2$—H), 5.08 (d, 1, J=4 Hz, C$_6$—H), 5.4-6.0 (mult, 2H, C$_7$—H and C$_\alpha$—H), 6.6-7.6 (ArH), 9.37 (m, 2H, 2—NH).

EXAMPLE 20

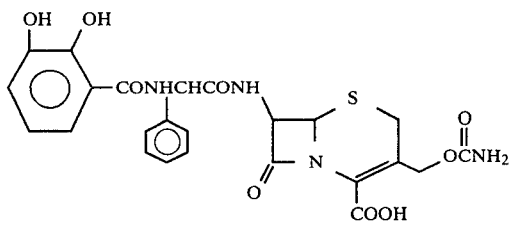

7-[D-[2-Phenyl-2-[(2,3-dihydroxybenzoyl-)amino]acetyl]amino]-3-carbamoyloxymethyl-3-cephem-4-carboxylic acid.

In accordance with the general procedures described in Example 1, 1 mmole of 7-phenylglycylamino-3-carbamoyloxymethyl-3-cephem-4-carboxylic acid trifluoroacetic acid said (derived by a trifluoroacetic acid cleavage of the corresponding t-BOC protected phenylglycyl amino cephem) was silylated with excess BSA and then acylated with 1 mmole of 1'-benzotriazolyl 2,3-dihydroxybenzoate. The title product was isolated in accordance with the isolation procedures described in Example 15 hereinabove. Yield-158.3 mg. (29%).

ir(KBr) 1760 cm$^{-1}$ ($\beta$-lactam C=O); uv(methanol) $\lambda$max 245 ($\epsilon$=13,550), 310 ($\epsilon$=3,400); Titration (66% DMF-34% water) pK$_a$=5.15, 8.70; nmr (DMSOd-6) $\delta$3.46 (broad s, 2H, C$_3$'—H), 4.55 (broad s, 2H, C$_2$—H), 5.08 (d, 1H, J=4.5 Hz, C$_6$—H), 5.5–6.0 (mult, 2H, C$_7$—H and C$_\alpha$—H), 6.55 (broad s, 2H, NH$_2$), 6.7–7.7 (ArH) and 9.40 (mult, 2H, 2—NH).

We claim:

1. The compound of the formula

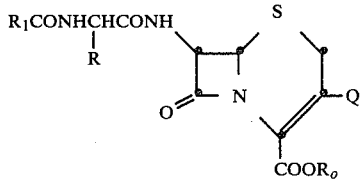

wherein Q is a group of the formula —CH$_2$R$_2$
wherein R$_2$ is
a group of the formula —SR$_3$
wherein R$_3$ is (a) a tetrazolyl group selected from the group consisting of

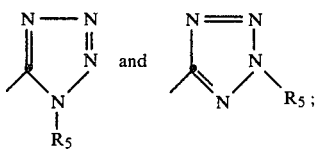

(b) a thiadiazolyl group selected from the group consisting of

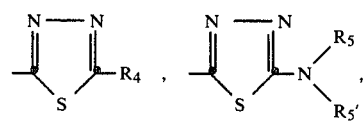

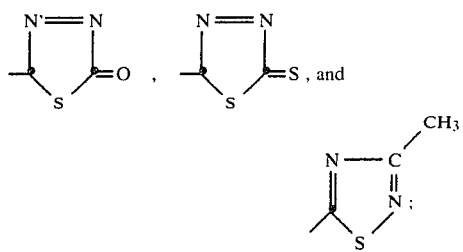

(c) an oxadiazolyl group of the formula

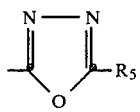

(d) a triazolyl group selected from the group consisting of

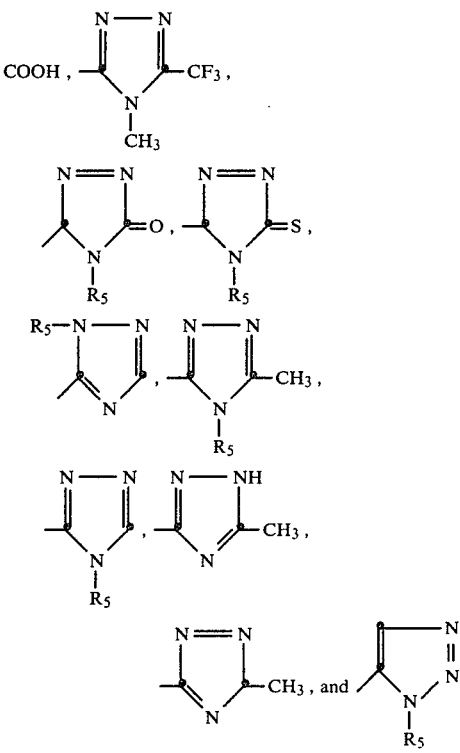

(e) a thiazolyl group selected from the group consisting of

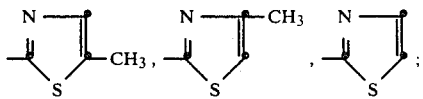

(f) an isothiazolyl group of the formula

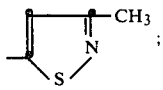

(g) an oxazolyl group of the formula

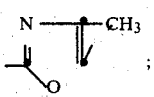

(h) a triazinyl group of the formula

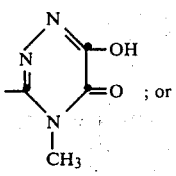

R₃ is

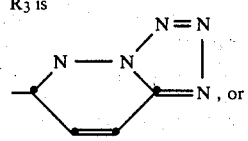

wherein in the above formulas R₄ is hydrogen, $C_1-C_4$ alkyl, aminomethyl, protected aminomethyl or hydroxymethyl, and $R_5$ and $R_5'$ are hydrogen or $C_1-C_4$ alkyl; and R is cyclohexadienyl, phenyl or phenyl substituted with 1 or 2 groups selected from the group consisting of $C_1-C_4$ alkyl, $C_1-C_4$ alkoxy, halo, hydroxy, protected hydroxy, nitro, cyano, methanesulfonamido and trifluoromethyl; or R is 2-thienyl, 3-thienyl, 2-furyl or 3-furyl; and $R_1$ is a group of the formula

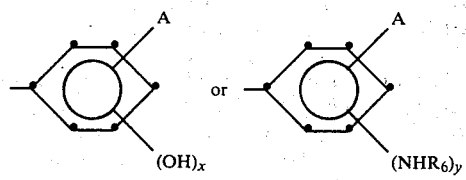

wherein X is 1, 2, or 3, and y is 1 or 2, and wherein A is a substituent selected from the group consisting of hydrogen, halo, $C_1-C_4$ alkoxy, amino, protected amino, hydroxy, protected hydroxy, $C_1-C_4$ alkyl, nitro, cyano, methanesulfonamido and trifluoromethyl, and $R_6$ is hydrogen or an amino protecting group; and $R_o$ is hydrogen, indanyl, phthalidyl or an acyloxymethyl group of the formula

CH₂OCY' wherein Y' is $C_1-C_4$ alkyl or phenyl; and when $R_o$ is hydrogen, the pharmaceutically acceptable nontoxic salts of the acids represented thereby.

2. The compound of claim 1 wherein $R_o$ is hydrogen and $R_1$ is a group of the formula

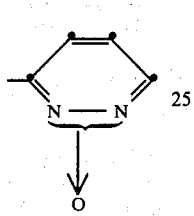

3. The compound of claim 2 wherein A and $R_6$ are hydrogen.

4. The compound of claim 3 said compound being 7-[D-[2-(4-hydroxyphenyl)-2-[(3,4-diaminobenzoyl)amino]-acetyl]amino]-3-[[(5-methyl-1,3,4-thiadiazol-2-yl)thio]-methyl]-3-cephem-4-carboxylic acid.

5. The compound of claim 1 wherein $R_o$ is hydrogen and $R_1$ is a group of the formula

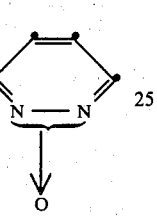

6. The compound of claim 5 wherein $R_1$ is a group of the formula

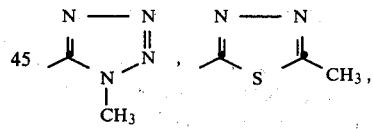

wherein A is hydrogen.

7. The compound of claim 6 wherein Q is a group of the formula $-CH_2SR_3$ wherein $R_3$ is

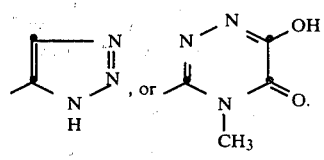

8. The compound of claim 6 wherein R is phenyl, 3-hydroxyphenyl, 4-hydroxyphenyl, 3-methanesulfonamidophenyl, 2-thienyl or 1,4-cyclohexadienyl.

9. The compound of claim 8 wherein R is phenyl or 4-hydroxyphenyl.

10. The compound of claim 9 wherein Q is a group of the formula $-CH_2SR_3$ wherein $R_3$ is

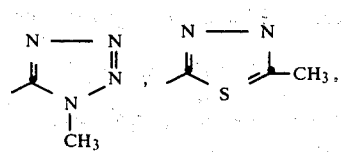

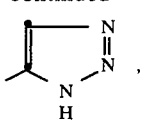 , 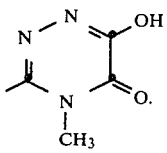 ,

11. The compound of claim 6 wherein R₁ is a group of the formula

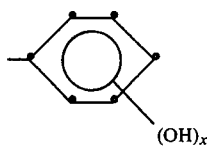

wherein X is 2 or 3 and wherein at least two of the hydroxy substituents are bonded to the phenyl at adjacent carbon atoms.

12. The compound of claim 11 wherein R is phenyl, 3-hydroxyphenyl, 4-hydroxyphenyl, 3-methanesulfonamidophenyl, 2-thienyl or 1,4-cyclohexadienyl.

13. The compound of claim 12 wherein Q is a group of the formula —CH₂SR₃ and R₃ is

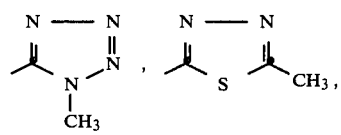

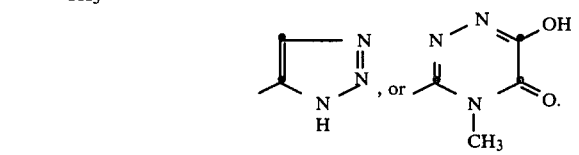

14. The compound of claim 13 wherein R is phenyl or 4-hydroxyphenyl.

15. The compound of claim 11 wherein R₁ is 2,3-dihydroxyphenyl, 3,4-dihydroxyphenyl, or 3,4,5-trihydroxyphenyl.

16. The compound of claim 15 wherein R is phenyl, 3-hydroxyphenyl, 4-hydroxyphenyl, 3-methanesulfonamidophenyl, 2-thienyl or 1,4-cyclohexadienyl.

17. The compound of claim 16 wherein Q is a group of the formula —CH₂SR₃ and R₃ is

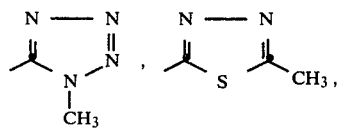

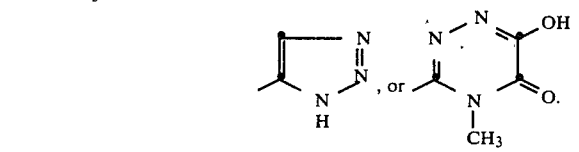

18. The compound of claim 17 wherein R is phenyl or 4-hydroxyphenyl.

19. The compound of claim 18 said compound being 7-[D-[2-phenyl-2-[(2,3-dihydroxybenzoyl)amino]acetyl]-amino]-3-[[(1-methyltetrazol-5-yl)thio]methyl]-3-cephem-4-carboxylic acid.

20. The compound of claim 18 said compound being 7-[D-[2-(4-hydroxyphenyl)-2-[(3,4-dihydroxybenzoyl)amino]-acetyl]amino]-3-[[(1-methyltetrazol-5-yl)thio]methyl]-3-cephem-4-carboxylic acid.

21. The compound of claim 18 said compound being 7-[D-[2-(4-hydroxyphenyl)-2-[(2,3-dihydroxybenzoyl)amino]-acetyl]amino]-3-[[(1-methyltetrazol-5-yl)thio]methyl]-3-cephem-4-carboxylic acid.

22. The compound of claim 18 said compound being 7-[D-[2-(4-hydroxyphenyl)-2-[(3,4,5-trihydroxybenzoyl)-amino]acetyl]amino]-3-[[(5-methyl-1,3,4-thiadiazol-2-yl)thio]methyl]-3-cephem-4-carboxylic acid.

23. The compound of claim 18 said compound being 7-[D-[2-(4-hydroxyphenyl)-2-[(3,4,5-trihydroxybenzoyl)-amino]acetyl]amino]-3-[[(1-methyltetrazol-5-yl)thio]methyl]-3-cephem-4-carboxylic acid.

24. The compound of claim 18 said compound being 7-[D-[2-(4-hydroxyphenyl)-2-[(2,3-dihydrobenzoyl)amino]-acetyl]amino]-3-[[(5-methyl-1,3,4-thiadiazol-2-yl)thio]-methyl]-3-cephem-4-carboxylic acid.

25. The compound of claim 18 said compound being 7-[D-[2-(4-hydroxyphenyl)-2-[(3,4-dihydroxybenzoyl)amino]-acetyl]amino]-3-[[(5-methyl-1,3,4-thiadiazol-2-yl)thio]-methyl]-3-cephem-4-carboxylic acid.

26. The compound of claim 18 said compound being 7-[D-[2-(4-hydroxyphenyl)-2-[(2,3-dihydroxybenzoyl)amino]-acetyl]amino]-3-[[(4,5-dihydro-6-hydroxy-4-methyl-5-oxo-1,2,4-triazin-3-yl)thio]methyl]-3-cephem-4-carboxylic acid.

27. The compound of claim 18 said compound being 7-[D-[2-(4-hydroxyphenyl)-2-[(3,4-dihydroxybenzoyl)amino]-acetyl]amino]-3-[[(4,5-dihydro-6-hydroxy-4-methyl-5-oxo-1,2,4-triazin-3-yl)thio]methyl]-3-cephem-4-carboxylic acid.

28. The compound of claim 18 said compound being 7-[D-[2-(4-hydroxyphenyl)-2-[(3,4,5-trihydroxybenzoyl)-amino]acetyl]amino]-3-[[(4,5-dihydro-6-hydroxy-4-methyl-5-oxo-1,2,4-triazin-3-yl)thio]methyl]-3-cephem-4-carboxylic acid.

29. The compound of claim 18 said compound being 7-[D-[2-phenyl-2-[(2,3-dihydroxybenzoyl)amino]acetyl]amino]-3-[[(5-methyl-1,3,4-thiadiazol-2-yl)thio]methyl]-3-cephem-4-carboxylic acid.

30. The compound of claim 18 said compound being 7-[D-[2-phenyl-2-[(2,3-dihydroxybenzoyl)amino]acetyl]amino]-3-[[(4,5-dihydro-6-hydroxy-4-methyl-5-oxo-1,2,4-triazin-3-yl)thio]methyl]-3-cephem-4-carboxylic acid.

31. The compound of claim 18 said compound being 7-[D-[2-phenyl-2-[(3,4-dihydroxybenzoyl)amino]acetyl]amino]-3-[[(4,5-dihydro-6-hydroxy-4-methyl-5-oxo-1,2,4-triazin-3-yl)thio]methyl]-3-cephem-4-carboxylic acid.

32. The compound of claim 18 said compound being 7-[D-[2-phenyl-2-[(3,4-dihydroxybenzoyl)amino]acetyl]amino]-3-[[(5-methyl-1,3,4-thiadiazol-2-yl)thio]methyl]-3-cephem-4-carboxylic acid.

33. The compound of claim 18 said compound being 7-[D-[2-phenyl-2-(3,4-dihydroxybenzoyl)amino]acetyl]amino]-3-[[(1-methyltetrazol-5-yl)thio]methyl]-3-cephem-4-carboxylic acid.

34. The compound of claim 18 said compound being 7-[D-[2-phenyl-2-[(3,4,5-trihydroxybenzoyl)amino]acetyl]-amino]-3-[[(1-methyltetrazol-5-yl)thio]methyl]-3-cephem-4-carboxylic acid.

35. The compound of claim 18 said compound being 7-[D-[2-phenyl-2-[(3,4,5-trihydroxybenzoyl- )amino]acetyl]-amino]-3-[[(5-methyl-1,3,4-thiadiazol-2-yl)thio]methyl]-3-cephem-4-carboxylic acid.

36. The compound of claim 18 said compound being 7-[D-[2-phenyl-2-[(3,4,5-trihydroxybenzoyl)amino]acetyl]-amino]-3-[[(4,5-dihydro-6-hydroxy-4-methyl-5-oxo-1,2,4-triazin-3-yl)thio]methyl]-3-cephem-4-carboxylic acid.

37. A compound of the formula

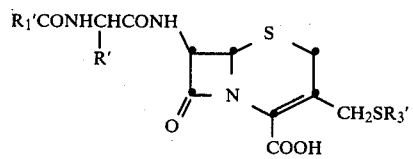

wherein

R' is phenyl, hydroxyphenyl or methanesulfonamidophenyl;

R'$_1$ is a group of the formula

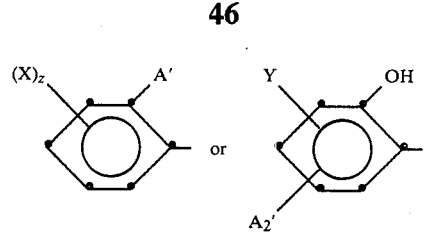

wherein

A' is hydroxy, halo, C$_1$–C$_4$ alkoxy, nitro or methanesulfonamido;
A'$_2$ is hydrogen, halo, nitro, or hydroxy.
X is amino or hydroxy;
Y is hydrogen or hydroxy; and
z is 1 or 2; and
R'$_3$ is selected from the group consisting of 1H-tetrazol-5-yl, 1-(C$_1$–C$_4$ alkyl)-tetrazol-5-yl, 2H-tetrazol-5-yl, 2-(C$_1$–C$_4$ alkyl)tetrazol-5-yl, 4H-1,2,4-triazol-3-yl, 4-(C$_1$–C$_4$ alkyl)-1,2,4-triazol-3-yl, 1H-1,2,3-triazol-5-yl, 1-(C$_1$–C$_4$ alkyl)-1,2,3-triazol-5-yl, 4-methyl-1,3-oxazol-2-yl, 1,2,4-oxadiazol-2-yl, 5-(C$_1$–C$_4$ alkyl)-1,2,4-oxadiazol-2-yl, 5-methylthiazol-2-yl, 4-methylthiazol-2-yl, thiazol-2-yl, 3-methylisothiazol-5-yl, 1,3,4-thiadiazol-2-yl, 5-(C$_1$–C$_4$ alkyl)-1,3,4-thiadiazol-2-yl, 5-aminomethyl-1,3,4-thiadiazol-2-yl, and 3-methyl-1,2,4-thiadiazol-5-yl;

and the pharmaceutically acceptable non-toxic salts thereof.

* * * * *